(12) United States Patent
Friedlander et al.

(10) Patent No.: US 11,523,728 B2
(45) Date of Patent: Dec. 13, 2022

(54) PEDIATRIC NASAL ENDOSCOPE, GASTROSCOPE AND AERODIGESTIVE SCOPE

(71) Applicant: The Regents of the University of Colorado, A Body Corporate, Denver, CO (US)

(72) Inventors: Joel Friedlander, Englewood, CO (US); Jeremy Prager, Englewood, CO (US); Emily Deboer, Denver, CO (US); Robin Deterding, Boulder, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 15/887,438

(22) Filed: Feb. 2, 2018

(65) Prior Publication Data

US 2018/0153373 A1 Jun. 7, 2018

Related U.S. Application Data

(63) Continuation of application No. 15/853,521, filed on Dec. 22, 2017, now abandoned, which is a
(Continued)

(51) Int. Cl.
*A61B 1/00* (2006.01)
*A61B 1/015* (2006.01)
(Continued)

(52) U.S. Cl.
CPC ........ *A61B 1/00006* (2013.01); *A61B 1/0004* (2022.02); *A61B 1/0005* (2013.01);
(Continued)

(58) Field of Classification Search
CPC . A61B 1/00006; A61B 1/233; A61B 1/00045; A61B 1/0052; A61B 1/015;
(Continued)

(56) References Cited

U.S. PATENT DOCUMENTS 5,474,063 A 12/1995 Riendeau ................. 128/207.18
5,624,379 A 4/1997 Ganz et al.
(Continued)

FOREIGN PATENT DOCUMENTS

EP 2416833 A2 2/2012
JP S50-075794 11/1948
(Continued)

OTHER PUBLICATIONS

Chheda, Neil N.; Postma, Greogry N.; "Transnasal Esophagoscopy"; Apr. 21, 2015; Clinical Gate, Chapter 73; https://clinicalgate.com/transnasal-esophagoscopy/ (Year: 2015).*
(Continued)

*Primary Examiner* — Michael J Carey
*Assistant Examiner* — Pamela F Wu
(74) *Attorney, Agent, or Firm* — J. Peter Paredes; Amin Talati Wasserman LLP

(57) ABSTRACT

TNE provides the opportunity to make the care of children with EoE and other gastrointestinal or aerodigestive conditions safer, more efficient, and less costly while simultaneously advancing our understanding of the pathophysiology and natural course of this condition. A pediatric endoscope was developed to facilitate TNE in children with EoE. The pediatric endoscope (combined gastroscope, bronchoscope, laryngoscope) includes a 3-4 mm flexible, fiber optic endoscope that allows HD TV viewing with the head of a pediatric bronchoscope that allows four way tip deflection, a scope stiffening apparatus to minimize the endoscopes flexibility when needed, a foot and hand activation to allow
(Continued)

air/water insufflation and image/video capture, a light source, 2 mm biopsy channel.

30 Claims, 28 Drawing Sheets

Related U.S. Application Data continuation of application No. PCT/US2016/039352, filed on Jun. 24, 2016.

(60) Provisional application No. 62/184,077, filed on Jun. 24, 2015.

(51) Int. Cl.
| | |
|---|---|
| *A61N 7/02* | (2006.01) |
| *A61B 1/005* | (2006.01) |
| *A61B 18/18* | (2006.01) |
| *A61B 1/233* | (2006.01) |
| *A61B 1/267* | (2006.01) |
| *A61J 15/00* | (2006.01) |
| *A61B 1/018* | (2006.01) |
| *A61B 10/06* | (2006.01) |
| *A61B 34/30* | (2016.01) |
| *A61B 1/273* | (2006.01) |
| *A61B 18/14* | (2006.01) |
| *A61B 18/00* | (2006.01) |
| *A61B 1/07* | (2006.01) |

(52) U.S. Cl.
CPC ...... *A61B 1/00039* (2013.01); *A61B 1/00045* (2013.01); *A61B 1/00048* (2013.01); *A61B 1/0052* (2013.01); *A61B 1/00066* (2013.01); *A61B 1/00078* (2013.01); *A61B 1/00174* (2013.01); *A61B 1/015* (2013.01); *A61B 1/018* (2013.01); *A61B 1/233* (2013.01); *A61B 1/2676* (2013.01); *A61B 1/2733* (2013.01); *A61B 10/06* (2013.01); *A61B 18/1815* (2013.01); *A61B 34/30* (2016.02); *A61J 15/0026* (2013.01); *A61N 7/022* (2013.01); *A61B 1/00013* (2013.01); *A61B 1/07* (2013.01); *A61B 18/1492* (2013.01); *A61B 2018/00488* (2013.01); *A61B 2018/00541* (2013.01); *A61B 2018/00577* (2013.01); *A61B 2018/00982* (2013.01); *A61B 2018/1861* (2013.01); *A61B 2018/1869* (2013.01); *A61B 2034/301* (2016.02); *A61B 2503/06* (2013.01)

(58) Field of Classification Search
CPC .. A61B 1/018; A61B 1/04; A61B 1/05; A61B 1/12; A61B 1/267; A61B 1/2676; A61B 1/00013; A61B 1/07; A61B 1/126; A61B 2018/00541; A61B 34/30; A61B 1/00039; A61B 1/00066; A61B 1/00078; A61B 1/00174
USPC ....... 600/101, 433, 435, 104, 129, 130, 139, 600/153
See application file for complete search history.

(56) References Cited

U.S. PATENT DOCUMENTS

| | | | |
|---|---|---|---|
| 6,241,657 B1 | 6/2001 | Chen et al. | |
| 9,179,051 B1 | 11/2015 | Stoudt | |
| 9,848,761 B2 | 12/2017 | Demers et al. | ........ A61B 1/07 |
| 2004/0176683 A1 | 9/2004 | Whitin et al. | ........ 600/424 |
| 2005/0197536 A1* | 9/2005 | Banik | ........ A61B 1/00059 600/179 |
| 2005/0235422 A1* | 10/2005 | Wallace | ........ A61B 5/055 5/601 |
| 2007/0167967 A1* | 7/2007 | Mikkaichi | ........ A61B 17/3421 606/185 |
| 2008/0154090 A1* | 6/2008 | Hashimshony | ........ A61B 1/018 600/104 |
| 2008/0262468 A1* | 10/2008 | Clifford | ........ A61F 11/002 604/501 |
| 2009/0318798 A1* | 12/2009 | Singh | ........ A61B 1/012 600/424 |
| 2010/0137688 A1 | 6/2010 | Couvillon, Jr. | |
| 2011/0146676 A1* | 6/2011 | Dallam | ........ A61B 90/35 128/203.12 |
| 2012/0209073 A1* | 8/2012 | McWeeney | ........ A61B 1/008 600/146 |
| 2013/0023770 A1* | 1/2013 | Courtney | ........ A61M 39/223 600/467 |
| 2013/0158451 A1 | 6/2013 | Juto et al. | ........ A61H 1/00 |
| 2013/0249787 A1 | 9/2013 | Morimoto | ........ G02B 27/0179 |
| 2014/0296633 A1 | 10/2014 | Gumbs et al. | |
| 2014/0320617 A1 | 10/2014 | Parks et al. | ........ A61B 1/00181 |
| 2015/0209055 A1* | 7/2015 | Chang | ........ A61B 17/24 600/424 |
| 2015/0253574 A1 | 9/2015 | Thurber | ........ G02B 27/0172 |
| 2015/0306340 A1* | 10/2015 | Giap | ........ G16H 40/63 600/301 |
| 2016/0135672 A1 | 5/2016 | Spinnler et al. | ........ A61B 1/06 |
| 2018/0055347 A1 | 3/2018 | Teixeira Dos Santos Paulo | ........ A61B 1/018 |
| 2018/0146839 A1 | 5/2018 | Friedlander et al. | ........ A61B 1/00006 |

FOREIGN PATENT DOCUMENTS

| | | | |
|---|---|---|---|
| JP | S60-182928 | 9/1985 | ........ A61B 1/04 |
| JP | H03-178631 | 8/1991 | ........ A61B 1/00 |
| JP | H11-032982 | 2/1999 | ........ A61B 1/04 |
| JP | 2001091892 A | 4/2001 | |
| JP | 2003-038421 | 2/2003 | ........ A61B 1/00 |
| JP | 2005-507273 | 3/2005 | ........ A61B 8/12 |
| JP | 2007-512099 | 5/2007 | ........ A61B 8/12 |
| JP | 2009-165632 | 7/2009 | ........ A61B 1/00 |
| JP | 2013-507189 | 3/2013 | ........ A61B 1/00 |
| WO | 2013/101912 | 7/2013 | |
| WO | 2016-210322 A1 | 12/2016 | |

OTHER PUBLICATIONS

International Search Report and Written Opinion of the International Searching Authority dated Sep. 14, 2016, which issued during prosecution of International Application No. PCT/US2016/039352.
International Search Report established for PCT/US2018/067152 dated Sep. 4, 2019.
International Search Report and Written Opinion issued in corresponding foreign application, PCT/US2019/034954, pp. 1-9 (dated Aug. 8, 2019).
International Search Report and Written Opinion issued in corresponding foreign application, PCT/US2019/051523, pp. 1-13 (dated Jan. 29, 2020).
Office Action issued in corresponding foreign application, JP2017-566710, pp. 1-3 (dated Aug. 11, 2020).
Office Action issued in corresponding foreign application, JP2017-566710, pp. 1-3 (dated Mar. 15, 2021).
Extended European Search Report issued in corresponding foreign application, EP18890819.8, 8 pages (dated Sep. 6, 2021).
European Patent Office, Extended European Search Report issued in related foreign application, EP119861561.9, 10 pages (dated Jun. 22, 2022).
Sony, "HMZ-T3W/HMZ-T3 Personal 3D Viewer", Nov. 9, 2013, Retrieved from the Internet: URL:http://web.archive.org/web/20131109115919/http://www.sony.jp/hmd/products/HMZ-T3, [retrieved on May 25, 2022], 1 page.

\* cited by examiner

SECTION A-A

6. APENDEX A SETUP SCREEN    4500

CHILDREN'S HOSPITAL COLORADO

PATIENT NAME

MRN

DATE OF BIRTH

SURGEON

ASSISTANT

PROCEDURE NAME

ACCEPT

FIG. 41

PEDIATRIC NASAL ENDOSCOPE, GASTROSCOPE AND AERODIGESTIVE SCOPE

CROSS-REFERENCE TO RELATED APPLICATIONS

This application is a continuation of U.S. application Ser. No. 15/853,521, which is a continuation-in-part of International Patent Application No. PCT/US2016/039352 filed Jun. 24, 2016, which published as PCT Publication No. WO 2016/210322 on Dec. 29, 2016, which claims the benefit of U.S. Provisional Application No. 62/184,077 filed on Jun. 24, 2015. The contents of each of the aforementioned patent applications are herein incorporated by reference in their entirety. U.S. application Ser. No. 15/853,521, to which this application claims priority, is also a continuation-in-part of U.S. application Ser. No. 15/850,939, which is a continuation of International Patent Application No. PCT/US2016/039352 filed Jun. 24, 2016, which published as PCT Publication No. WO 2016/210322 on Dec. 29, 2016, which claims the benefit of U.S. Provisional Application No. 62/184,077 filed on Jun. 24, 2015.

BACKGROUND OF THE INVENTION

1. Field of Invention

This invention relates to the evaluation and treatment of eosinophilic esophagitis, esophagitis, and aerodigestive conditions in children. More specifically, this invention relates to pediatric nasal endoscopes.

2. Brief Description of the Related Art

Eosinophilic esophagitis (EoE) is an increasingly common chronic inflammatory disease that affects children and adults with an estimated incidence of 1/10,000 in the United States. [Dellon E S, Gonsalves N, Hirano I, et al. ACG clinical guideline: Evidenced based approach to the diagnosis and management of esophageal eosinophilia and eosinophilic esophagitis (EoE). *Am J Gastroenterol* 2013; 108: 679-92; quiz 693] Because of its potential to progress to esophageal stricture and the fact that symptoms do not always correlate with degree of eosinophilia, much attention has been paid to repeated assessment of the esophageal mucosa to insure mucosal healing following treatment. In contrast, the risks, cost and time commitment associated with traditional sedated esophagogastroduodenoscopy (EGD) can be significant and have raised concerns for providers and parents alike. [Gleich S J, Flick R, Hu D, et al. Neurodevelopment of children exposed to anesthesia: Design of the Mayo Anesthesia Safety in Kids (MASK) study. *Contemp Clin Trials* 2014; 41C:45-54] These dilemmas challenge the gastroenterologist to contemplate if EGD use in EoE is meeting the goal of Berwick's triple aim in health care to provide effective treatment, low cost care, and an optimal and safe healthcare experience. [Berwick D M, Nolan T W, Whittington J. The triple aim: care, health, and cost. *Health Aff (Millwood)* 2008; 27:759-69] Should EGD with biopsy be performed after each therapeutic change regardless of symptomatology, should EGD be reserved for patients who are not clinically responding to treatment, or should EGD not be performed again if patients are feeling well?

To address these questions, alternative methods are urgently needed to measure esophageal inflammation. While esophagoscopy with biopsies remains the gold standard technique for assessing mucosal inflammation, other technologies such as the Cytosponge, esophageal string test and confocal tethered endomicroscopy have emerged as potential alternatives. [Furuta G T, Kagalwalla A F, Lee J J, et al. The oesophageal string test: a novel, minimally invasive method measures mucosal inflammation in eosinophilic oesophagitis. *Gut* 2013; 62:1395-405; Tabatabaei N, Kang D, Wu T, et al. Tethered confocal endomicroscopy capsule for diagnosis and monitoring of eosinophilic esophagitis. *Biomed Opt Express* 2013; 5:197-207; Katzka D A, Geno D M, Ravi A, et al. Accuracy, safety, and tolerability of tissue collection by Cytosponge vs endoscopy for evaluation of eosinophilic esophagitis. *Clin Gastroenterol Hepatol* 2015; 13:77-83 e2.] To date, these tools, while less invasive, are still available only in research settings. [Dellon E S, Gonsalves N, Hirano I, et al. *Am J Gastroenterol* 2013; 108: 679-92; quiz 693; Furuta G T, Kagalwalla A F, Lee J J, et al., *Gut* 2013; 62:1395-405]

Recent work has lead to the development of transnasal endoscopy/esophagoscopy (TNE) to assess the esophageal mucosa in adults. [Birkner B, Fritz N, Schatke W, et al. A prospective randomized comparison of unsedated ultrathin versus standard esophagogastroduodenoscopy in routine outpatient gastroenterology practice: does it work better through the nose? *Endoscopy* 2003; 35:647-51; Dumortier J, Josso C, Roman S, et al. Prospective evaluation of a new ultrathin one-plane bending videoendoscope for transnasal EGD: a comparative study on performance and tolerance. *Gastrointest Endosc* 2007; 66:13-9; Dumortier J, Ponchon T, Scoazec J Y, et al. Prospective evaluation of transnasal esophagogastroduodenoscopy: feasibility and study on performance and tolerance. *Gastrointest Endosc* 1999; 49:285-91; Hu C T. Gauze pledgetting versus endoscopic-guided aerosolized spray for nasal anesthesia before transnasal EGD: a prospective, randomized study. *Gastrointest Endosc* 2010; 71:11-20; Mokhashi M S, Wildi S M, Glenn T F, et al. A prospective, blinded study of diagnostic esophagoscopy with a superthin, stand-alone, battery-powered esophagoscope. *Am J Gastroenterol* 2003; 98:2383-9; Mulcahy H E, Riches A, Kiely M, et al. A prospective controlled trial of an ultrathin versus a conventional endoscope in unsedated upper gastrointestinal endoscopy. *Endoscopy* 2001; 33:311-6; Yagi J, Adachi K, Arima N, et al. A prospective randomized comparative study on the safety and tolerability of transnasal esophagogastroduodenoscopy. *Endoscopy* 2005; 37:1226-31] In contrast to traditional EGDs, TNE offers advantages including that it can be performed in an outpatient clinic room, requires no anesthesia or sedation, uses an adult transnasal gastroscope that is tolerated by adults and procures samples adequate for assessment of Barrett's Esophagus. [Shariff M K, Bird-Lieberman E L, O'Donovan M, et al. Randomized crossover study comparing efficacy of transnasal endoscopy with that of standard endoscopy to detect Barrett's esophagus. *Gastrointest Endosc* 2012; 75:954-61; Saeian K, Staff D M, Vasilopoulos S, et al. Unsedated transnasal endoscopy accurately detects Barrett's metaplasia and dysplasia. *Gastrointest Endosc* 2002; 56:472-8] However, the endoscopes used in the adult procedures are not appropriate for use in pediatric setting. Adult endoscopes have a large bulky head, will not fit in many pediatric size nasal passages, do not have stiffening capability for improve maneuverability, do not have foot controls, are not able to be used in pediatrics, and are unable to be used for bronchoscopy. Accordingly, what is needed is a device and associated methodology that can be used to adapt TNE to assess the esophageal mucosa, gastric, and duodenal, tracheal, and bronchial mucosa in children. The present invention provides tools and techniques to meet this important need.

BRIEF SUMMARY OF THE INVENTION

The long-standing but heretofore unfulfilled need for is now met by a new, useful, and nonobvious pediatric nasal endoscope. The invention includes a miniaturized 3-4 mm flexible, fiber optic endoscope approximately 1 meter in length that allows high resolution, high definition, and clear optics of the nasal mucosa, pharynx and upper gastrointestinal tract with the small head of a pediatric bronchoscope that allows four way tip deflection to allow use by individuals with small hand sizes, a foot pedal to allow air/water insufflation for ease of use, a bright light source, a scope stiffening apparatus that will allow utilization in aerodigestive medicine (combined ENT-laryngoscopy, Pulmonary (bronchoscopy), and Gastroenterology (EGD) Procedures) and a 2 mm biopsy channel to assure utilization of currently available endoscopic tools.

Unsedated laryngoscopy in pediatric otolaryngology and pediatric pulmonology has been performed in pediatric patients. [Wood R E. Evaluation of the upper airway in children. *Curr Opin Pediatr* 2008; 20:266-71] We hypothesized that TNE could be adapted to provide a safe and effective tool to monitor and sample the mucosa of children with EoE. Ultra-slim flexible endoscopes were developed to create instruments that could be tolerated by children, while still allowing for the removal of adequate samples. This scope design is unique in that it can be used in pediatric nasal endoscopy, pediatric nasal bronchoscopy, and pediatric laryngoscopy. This design differs from current adult nasal endoscopes in production in terms of numerous aspects including that that it is narrower, lighter, clearer, has foot controls, has smaller accessible hand controls to control the tip and be easier to maneuver. This scope will also have a stiffening capability and narrow tip to allow it to be used in aerodigestive medicine and other medical and surgical specialties. The present disclosure documents the performance of TNE with biopsies using these ultra-slim flexible endoscopes to assess the esophageal, gastric, duodenal, tracheal, and bronchial mucosa in pediatric subjects with EoE. The performance was assessed in part through the evaluation of parental and patient subject responses to TNE, the assessment of the ability to procure samples that would be adequate to monitor disease, monitoring adverse events, and recording procedure duration and charges generated. This assessment showed that unsedated transnasal endoscopy using the pediatric nasal endoscope disclosed herein offers an excellent alternative to sedated esophagogastroduodenoscopy.

Unsedated transnasal endoscopy (TNE) in adults is safer and less costly than sedated esophagogastroduodenoscopy (EGD). TNE with biopsies can be adapted as an effective tool to monitor the esophageal, gastric, and duodenal mucosa of children with eosinophilic esophagitis (EoE) or other conditions of the upper gastrointestinal tract with the proper tools and techniques. This technique can dramatically increase the safety and decrease cost in the care of children. The present disclosure documents the development of the performance of TNE with biopsies in pediatric EoE.

Subjects between 8 and 17 years of age with EoE, and their parents, were enrolled in the study. Unsedated TNE was performed. The currently available smaller endoscopes designed for bronchoscopy as a 2.8 mm (1.2 mm channel) or a 4 mm flexible bronchoscope (2 mm channel) were used, and esophageal biopsies were procured. These scopes were shorter than our currently proposed pediatric nasal endoscope and were without water channels, suction, air, foot control, high definition optics, or stiffening capability. Biopsy analysis, duration, adverse events, and billing charges of TNE were assessed. Immediately after TNE and a minimum of 2 weeks later, the mGHAA-9 (modified Group Health Association of America) and a preference questionnaire were completed, respectively.

Twenty-one of 22 enrolled subjects completed TNE. TNE was tolerated with no significant adverse events. Histopathological analysis revealed 0 eos/hpf (n=12), <15 eos/hpf (n=4), and >15 eos/hpf (n=5) and total epithelial surface area of mucosal biopsies samples from either TNE forceps compared to those obtained with standard endoscopic forceps was not statistically different. All parents and 76.2% of subjects would undergo the TNE again. TNE was preferred over EGD by 85.7% of parents and 52.4% of subjects. mGHAA-9 revealed a high degree of satisfaction (average 43.19+/−2.6 maximum score-45). Charges associated with TNE were 60.1% less than previous EGDs. The results of this study show that unsedated TNE is a preferred, efficacious, and lower cost procedure when monitoring esophageal mucosa of children with EoE.

In a first aspect the present invention provides an endoscope for assessment of the esophageal mucosa in children. The endoscope can have a flexible endoscope shaft having a first end, a second end, a length of about 0.8 meters to about 1.3 meters (preferably about 0.9 meters to about 1.2 meters, more preferably about 1.0 meters to about 1.1 meters, or about 1.05 meters), an outer diameter of between about 3.0 mm to about 4.0 mm (preferably about 3.0 mm to about 5.0 mm, more preferably about 3.25 mm to about 4.0 mm, about 3.5 mm to about 4.0 mm, about 3.5 mm, or about 4.0 mm) and having an inner channel lumen of about 1.5 mm to about 2.5 mm in diameter (preferably about 1.75 mm to about 2.25 mm, or about 2.0 mm). The lumen extends substantially the length of the shaft, and will generally have an opening at the distal-most portion of the second end to allow a surgical instrument to partially exit the lumen for placement of the tool in proximity to a tissue of interest. The shaft can be configured to facilitate irrigation and suction at the second end of the shaft, such as by including connection to a source for an irrigation liquid and/or suction and passage across the shaft of the endoscope for the liquid and its return. The endoscope according to the first aspect has a handle disposed at first end of the shaft. The handle can have a single or dual control to adjust the disposition of the second end of the shaft. The control enables four-way tip deflection of the second end of the shaft. This allows a user to direct the distal end of the shaft to facilitate visualization and sampling of desired tissues at the distal or second end. The endoscope according to the first aspect has an image sensor at the second end of the shaft. The image sensor facilitates imaging of tissues at the distal end of the endoscope when the endoscope is inserted within a cavity of a subject. The endoscope according to the first aspect has a light source disposed at the second end of the shaft to illuminate the area surrounding the distal end of the shaft.

In an advantageous embodiment the endoscope according to the first aspect can have a foot pedal or hand control to actuate suction or irrigation of the endoscope. The control can be integral to the handle to actuate suction or irrigation of the endoscope. In further embodiments the endoscope according to the first aspect can have a camera to facilitate visualization within the cavity of the subject. The image sensor can be a charge-coupled device (CCD) sensor, a complementary metal-oxide-semiconductor (CMOS) sensor, N-type metal-oxide-semiconductor (NMOS) sensor or a high definition video chip.

In an advantageous embodiment the endoscope according to the first aspect can have a scope shaft stiffening component. The scope shaft stiffening component can be used to selectively reduce the flexibility of the scope shaft. In other words, a user can selectively alter the stiffness of the shaft during use to suit the particular stiffness needed to execute a procedure or direct the placement of the shaft. The scope shaft stiffening component can be adapted to facilitate the use of the endoscope in aerodigestive medicine. Additionally, the lumen can have an opening at the distal-most end of the second end of the shaft. This allows for the passage of instruments and for the irrigation and suction of biological tissues through the length of the shaft and their partial exit from the shaft.

In a second aspect the present invention provides an endoscope for transnasal endoscopy in children. The endoscope according to the second aspect has a flexible endoscope shaft having a first end and a second end and has a diameter dimensioned for insertion into the nasal cavity of a child, a length of about 0.8 meters to 1.2 meters, and has an inner channel lumen configured to receive an elongate surgical instrument, the lumen extending substantially the length of the shaft. The shaft is configured to facilitate irrigation and suction at the second end of the shaft. The endoscope according to the second aspect has a handle disposed at the first end of the shaft, the handle including a single or dual control to adjust the disposition of the second end of the shaft thereby enabling four-way tip deflection. The endoscope according to the second aspect also has an image sensor at the second end of the shaft to facilitate imaging at the distal end of the endoscope when the endoscope is inserted within the nasal cavity of a subject. Lastly, the endoscope according to the second aspect has a light source disposed at the second end of the shaft to illuminate the area surrounding the distal end of the shaft.

In an advantageous embodiment the endoscope according to the second aspect can have a foot pedal or hand control to actuate suction or irrigation of the endoscope. The control can be integral to the handle to actuate suction or irrigation of the endoscope. In further embodiments the endoscope according to the second aspect can have a camera to facilitate visualization within the cavity of the subject. The image sensor can be a charge-coupled device (CCD) sensor, a complementary metal-oxide-semiconductor (CMOS) sensor, N-type metal-oxide-semiconductor (NMOS) sensor or a high definition video chip.

In an advantageous embodiment the endoscope according to the second aspect can have a scope shaft stiffening component. The scope shaft stiffening component can be adapted to facilitate the use of the endoscope in aerodigestive medicine. Additionally, the lumen can have an opening at the distal-most end of the second end of the shaft. This allows for the passage of instruments through the length of the shaft and their partial exit from the shaft.

In a third aspect the present invention provides a second endoscope for transnasal endoscopy in children. The endoscope according to the third aspect has a flexible endoscope shaft having a first end, a second end, a shaft diameter dimensioned for insertion into the nasal cavity of a child, a shaft length adapted to facilitate insertion of the shaft through the nasal cavity to the esophageal mucosa of a child, and an inner channel lumen configured to receive an elongate surgical instrument. The lumen extends substantially the length of the shaft. The shaft is further configured to facilitate irrigation and suction at the second end of the shaft. The endoscope according to the third aspect has a handle disposed at first end of the shaft. The handle has a single or dual control to adjust the disposition of the second end of the shaft thereby enabling four-way tip deflection. The endoscope according to the third aspect also has an image sensor at the second end of the shaft to facilitate imaging at the distal end of the endoscope when the endoscope is inserted within the nasal cavity of a subject. In addition, the endoscope according to the third aspect has a light source disposed at the second end of the shaft to illuminate the area surrounding the distal end of the shaft.

In an advantageous embodiment the endoscope according to the third aspect can have a foot pedal or hand control to actuate suction or irrigation of the endoscope. The control can be integral to the handle to actuate suction or irrigation of the endoscope. In further embodiments the endoscope according to the third aspect can have a camera to facilitate visualization within the cavity of the subject. The image sensor can be a charge-coupled device (CCD) sensor, a complementary metal-oxide-semiconductor (CMOS) sensor, N-type metal-oxide-semiconductor (NMOS) sensor or a high definition video chip.

In an advantageous embodiment the endoscope according to the third aspect can have a scope shaft stiffening component. The scope shaft stiffening component can be adapted to facilitate the use of the endoscope in aerodigestive medicine. Additionally, the lumen can have an opening at the distal-most end of the second end of the shaft. This allows for the passage of instruments through the length of the shaft and their partial exit from the shaft.

BRIEF DESCRIPTION OF THE DRAWINGS

For a fuller understanding of the invention, reference should be made to the following detailed description, taken in connection with the accompanying drawings, in which:

FIG. 41 is a screenshot of a setup display for the system.

DETAILED DESCRIPTION OF THE PREFERRED EMBODIMENT

Figure 1:
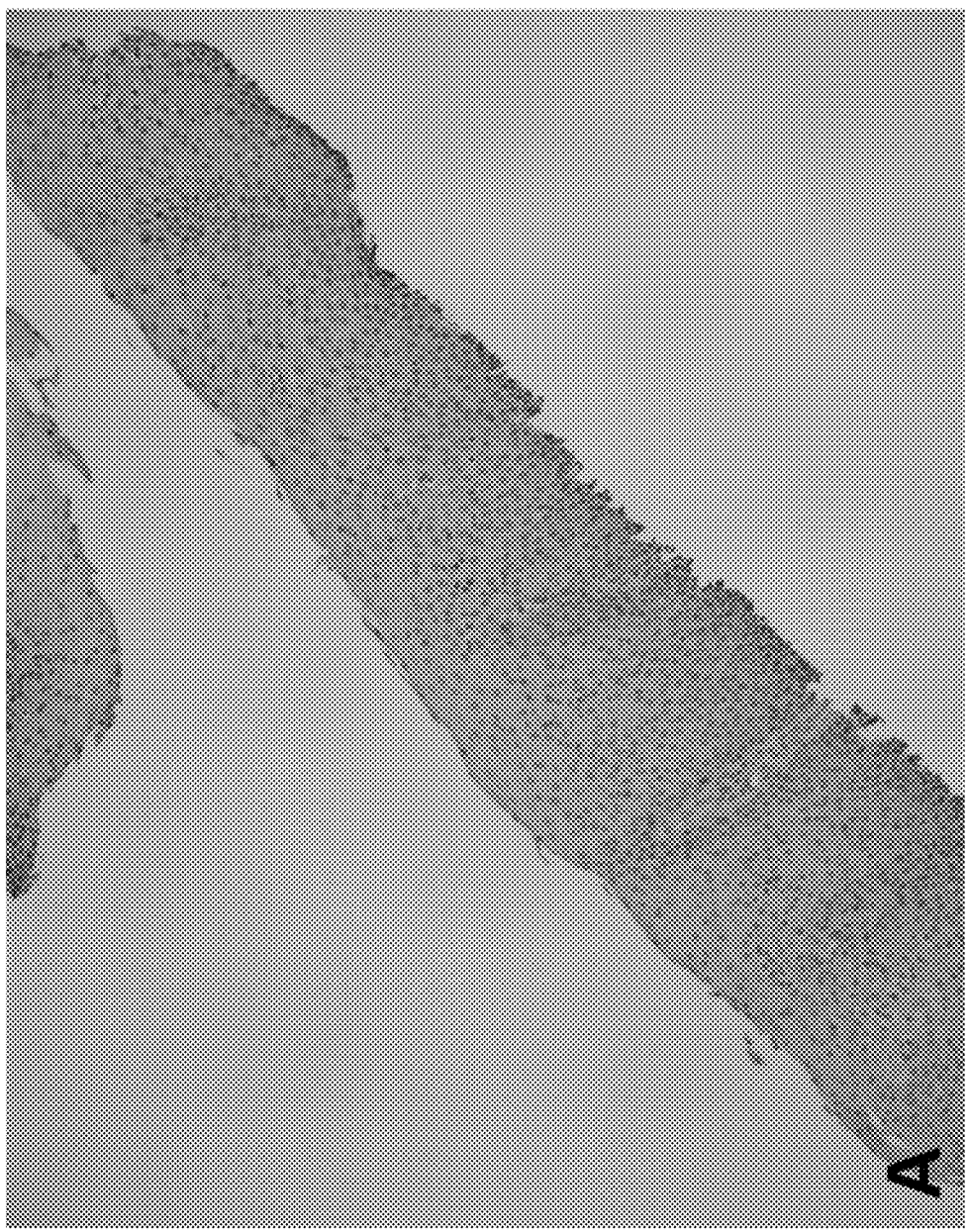
FIG. 1 is an image showing a biopsy with active EoE using a standard 2.8 mm EGD forceps. The surface area is 0.10 mm$^2$.
Figure 2:
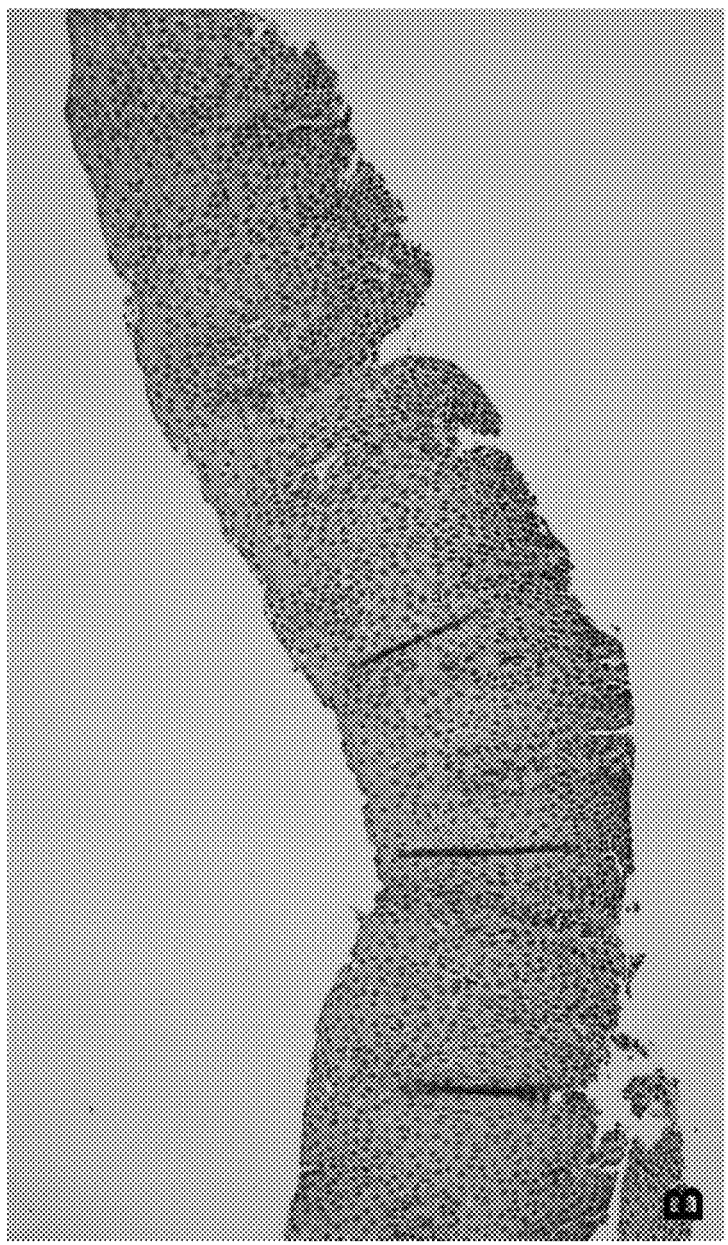
FIG. 2 is an image showing a biopsy from the same patient with active EoE using TNE 1.2 mm forceps. The surface area is 0.12 mm$^2$.

The emergence of EoE has led to a renewed interest in determining pathogenic mechanisms of esophageal inflammation and sampling of the esophageal mucosa to assess for mucosal healing. Despite the rapid progress in establishing diagnostic criteria, treatments, and novel genes related to pathogenic mechanisms that can significantly impact EoE patients, limited data is available to document the natural history of EoE. This lack of understanding has led to the present clinical practice of multiple, high-cost, and higher-risk sedated assessments of the esophageal mucosa to ascertain whether eosinophilia has resolved following treatment. If eosinophilia resolves, a predicate determination is made that the likelihood for EoE-related complications is diminished. If eosinophilia persists, efforts are made to resolve inflammation regardless of symptomatology, with its subsequent impact on quality of life and costs of care. In this regard, novel devices and sampling methodologies are urgently needed. To address this and offer a new tool in the evaluation of EoE, we sought to determine if TNE could sample the esophageal mucosa in a way that was well-tolerated and adequate. In light of the emergent need for more efficient methods of esophageal mucosal evaluation in EoE, we performed this study within the confines of a multi-disciplinary team to perform TNE with biopsies in a pediatric population. We chose this population because of the urgent need to minimize the repetitive risks of anesthesia, improve the understanding of EoE pathogenesis, and to ultimately identify novel therapeutic targets.

Unsedated TNE is an established technique in a number of pediatric and adult subspecialties, but it has not been used by pediatric gastroenterologists. [Birkner B, Fritz N, Schatke W, et al. *Endoscopy* 2003; 35:647-51; Dumortier J, Josso C, Roman S, et al. *Gastrointest Endosc* 2007; 66:13-9; Dumortier J, Ponchon T, Scoazec J Y, et al. *Gastrointest Endosc* 1999; 49:285-91; Hu C T. *Gastrointest Endosc* 2010; 71:11-20; Mokhashi M S, Wildi S M, Glenn T F, et al. *Am J Gastroenterol* 2003; 98:2383-9; Mulcahy H E, Riches A, Kiely M, et al. *Endoscopy* 2001; 33:311-6; Yagi J, Adachi K, Arima N, et al. *Endoscopy* 2005; 37:1226-31X] A number of studies have described the advantages, limitations, and challenges of TNE use, and in 2010, the America Society of Gastrointestinal Endoscopy developed a guideline for the use of TNE in adults. [Committee A T, Rodriguez S A, Banerjee S, et al. Ultrathin endoscopes. *Gastrointest Endosc* 2010; 71:893-8; Faulx A L, Catanzaro A, Zyzanski S, et al. Patient tolerance and acceptance of unsedated ultrathin esophagoscopy. *Gastrointest Endosc* 2002; 55:620-3; Faulx A L, Vela S, Das A, et al. The changing landscape of practice patterns regarding unsedated endoscopy and propofol use: a national Web survey. *Gastrointest Endosc* 2005; 62:9-15; Tatsumi Y, Harada A, Matsumoto T, et al. Current status and evaluation of transnasal esophagogastroduodenoscopy. *Dig Endosc* 2009; 21:141-6] This guideline increased attention to cost containment, and the recent upswing in interest in esophageal diseases led to renewed interest in this technique. [Faulx A L, Catanzaro A, Zyzanski S, et al. *Gastrointest Endosc* 2002; 55:620-3; Chak A, Alashkar B M, Isenberg G A, et al. Comparative acceptability of transnasal esophagoscopy and esophageal capsule esophagoscopy: a randomized, controlled trial in veterans. *Gastrointest Endosc* 2014; 80:774-82; Lin L F, Shen H C. Unsedated transnasal percutaneous endoscopic gastrostomy carried out by a single physician. *Dig Endosc* 2013; 25:130-5; Cho S, Arya N, Swan K, et al. Unsedated transnasal endoscopy: a Canadian experience in daily practice. *Can J Gastroenterol* 2008; 22:243-6] A recent study also demonstrated the utility of TNE in adult's with Barrett's esophagus. [Tatsumi Y, Harada A, Matsumoto T, et al. Current status and evaluation of transnasal esophagogastroduodenoscopy. *Dig Endosc* 2009; 21:141-6; Chak A, Alashkar B M, Isenberg G A, et al. Comparative acceptability of transnasal esophagoscopy and esophageal capsule esophagoscopy: a randomized, controlled trial in veterans. *Gastrointest Endosc* 2014; 80:774-82; Bush C M, Postma G N. Transnasal esophagoscopy. *Otolaryngol Clin North Am* 2013; 46:41-52]. To date, only one study evaluated unsedated trans oral endoscopy in children and concluded that it improved time and safety in assessing 21 children for evaluation of abdominal pain, dyspepsia, and dysphagia. [Bishop P R, Nowicki M J, May W L, et al. Unsedated upper endoscopy in children. *Gastrointest Endosc* 2002; 55:624-30]

With the rapidly increasing prevalence of EoE, limited knowledge regarding its pathophysiology, and emerging clinical needs to assess the esophageal mucosa, we sought to determine whether TNE in pediatric EoE would be a feasible and efficacious tool. Results of our study reveal that patients and parents experienced with sedated EGD tolerate TNE well, and that patients and their parents prefer TNE compared to EGD. It is likely that the limited side effect profile and complete lack of serious adverse events contributed to the finding that 52.4% of child subjects (4 subjects preferring neither EGD or TNE) and the 85.7% of parents (1 parent preferring neither TNE or EGD) preferred unsedated TNE to sedated EGD. In that parents often make decisions about procedures in pediatrics and a majority of children prefer the procedure, these percentages are indicative of a highly successful alternative to EGD. Immediate benefits of this preference for patients include improved patient satisfaction and increased safety by eliminating anesthesia.

In many ways our results are quite similar to that reported in adult studies. For example, a large Canadian Study by Cho et al. evaluating 231 patients with an average age of 57 years for routine TNE; their study also found that TNE was well tolerated, safe and feasible. [Cho S, Arya N, Swan K, et al. Unsedated transnasal endoscopy: a Canadian experience in daily practice. *Can J Gastroenterol* 2008; 22:243-6] This study was different, however, in that the patients were primarily adults, the scope used was larger (5.3 mm) and duodenal intubation was performed. Our study evaluated the use of 2 smaller endoscopes, smaller biopsy forceps, and TNE performance in children. Some areas of divergence between our findings and similar adult studies include that (1) in our study both the parents and child subjects evaluated the technique, (2) the adequacy of smaller forceps to evaluate the esophageal mucosa in EoE was assessed, and (3) the actual rather than contemplative type of future endoscopy preferred by subjects who have undergone multiple previous EGD's was examined. These findings augment the results of this research and its potential application to adult and pediatric endoscopy practices.

We are particularly encouraged by our findings for several reasons. First, there was great interest in this procedure amongst patients and parents. We only needed to screen 22 subjects to enroll the 21 subjects reported here. This is likely explained by the fact that the EoE patient population represents a very engaged, experienced, and educated population that is readily seeking alternative methods. We are highly confident that this is a technically feasible procedure, and are further encouraged by its overall rapid success that was facilitated by a multidisciplinary pediatric team dedicated to the care of children with aerodigestive diseases and EoE. Our study provides strong support for larger studies to validate this approach that will provide novel insights into the natural history of EoE and significantly improve the lives of children with EoE in a safer, cost effective, and efficacious manner.

Second, our study found a high level of satisfaction and enthusiasm to repeat the TNE. The overwhelming majority of patients and parents were satisfied and preferred unsedated TNE compared to standard EGD. Subject responses in the qualitative survey identified critical elements including the lack of anesthesia, the presence of parents during the procedure, the limited duration of the procedure and rapid recovery. TNE was safe, as evidenced by the fact that no significant adverse events or event needed subsequent treatment or evaluation. The subjects and parents appreciated the improvement in their quality of life with TNE, as it allowed them the ability to return to school and work and eat shortly afterwards. In fact, several families noted the patients returned to school or a sport activity after the TNE. The time at CHCO for a standard EGD is 3 hours compared to 60-90 minutes for the TNE, a time that included not only the TNE but also research protocol documentation. This 3-hour procedure center time for EGD usually includes check in, pre-operative evaluation by nursing, gastroenterology, and anesthesia, the procedure itself, recovery, and discharge instructions. The 60-90 minute time for TNE in clinic included research documentation, pre-procedural documentation, the procedure itself, and discharge instructions. Most of these improvements in time reduction and increased satisfaction, noted above, are related to the effects of eliminating anesthesia or sedation for TNE. Not only does this practice seem to improve satisfaction of patients and parents, but there is also a significant likelihood it decreases the risk of adverse medication reactions, aspiration, and possible effects on the developing pediatric brain. [Gleich S J, Flick R, Hu D, et al. *Contemp Clin Trials* 2014; 41C:45-54] This is an emerging concern amongst pediatric anesthesiologists. While pediatric subjects without sedation or general anesthesia noted a mild sore throat and gagging, this was minor enough that the majority chose follow up TNE for their EoE evaluation after their initial study procedure. This has been confirmed as more than a hypothetical question, with several of our subjects requesting follow up TNE after the study concluded.

The third positive outcome of our study relates to the integrity of the mucosal sample. Regarding the techniques effectiveness in evaluating mucosal esophageal sample, we found that the epithelial surface area needed for eosinophil count evaluation was not significantly different from the standard EGD 2.8 mm biopsy forceps compared to either of the TNE 2 mm or 1.2 mm biopsy forceps. This finding provides a high level of confidence that the sample procured at the time of TNE will have the same surface area compared to that obtained with the gold standard EGD biopsy forceps. The 2 mm forceps were also able to procure lamina propria.

The final areas of interest in this study were the reduction in cost and increase in efficiency. Financial benefits of TNE include the fact that TNE incurred fewer charges and required less time away from work and school when compared to a standard sedated pediatric EGD. The project demonstrated a significant 60.1% drop in charges. The majority of this reduction in cost is related to the lack of anesthetic/anesthesiologist during TNE. The significance of this cannot be understated. For example, if our institution were to perform 100 sedated EGD's per year for EoE at a hypothetical average, non-insurance adjusted charge of $9,390 dollars per general anesthesia provided endoscopy encounter, this would accumulate $939,000 total charges per year for EoE. This would include all facility charges, physician, pathology and anesthesia fees. If these 100 EGDs for EoE were converted to unsedated TNE, this could translate to a healthcare systems charge savings of $564,000 dollars per year. These are possible charges however and not respective insurance rates.

Several areas will be addressed in future evaluations. First, for practical reasons, we needed to use 2 different sized endoscopes for TNE. Future work will standardize this for patient comfort and biopsy size. Second, although the 1.2 mm forceps were not able to procure lamina propria, the 2 mm forceps in this study were able to obtain lamina propria. While this section of the tissue has been used to grade fibrosis, this metric has not been standardized or become a gold standard for clinical assessments. Our study demonstrates feasibility in pediatrics, but evaluating a much larger cohort is required to achieve a significant power for safety and other metrics. Power analysis based on our own institution's quality and safety data would necessitate over 10,000 endoscopies to find a single significant adverse event. This could be remedied with the development of further databases, as this technique is increasingly used at our institution or in a national program evaluating its use in pediatrics. Finally, we undertook this study in a multi-disciplinary collaboration with our pediatric pulmonary and otolaryngology colleagues. This was done for study design to maximize patient comfort during TNE development in pediatrics, a strong interest in aerodigestive and eosinophilic disorders by gastroenterologists, otolaryngologists, and pulmonologists alike, and the need for a more pragmatic multi-disciplinary approach to diagnosing and managing EoE as it presents in different single specialty clinics. Since the study initiation, the gastroenterologist, otolaryngologist, and pulmonologists have been trained in single physician TNE with biopsies that further improves cost and efficiency, diagnosis, and referral for management of EoE.

In conclusion, the implementation of TNE in pediatric gastroenterology for the evaluation of pediatric EoE is safe, preferred by patients and parents alike, and has the potential to dramatically reduce costs. Thus it appears that TNE would be measured as a highly effective practice in pediatric EoE management per Berwick's description of the triple aim: the pursuit of improved experience of care, the health of populations should be improved, and the cost of per capita healthcare should be decreased. [Berwick D M, Nolan T W, Whittington *J. Health Aff (Millwood)* 2008; 27:759-69] This suggests that TNE use should be highly considered as an alternative to standard sedated EGD or esophagoscopy for the follow up evaluation of pediatric EoE. The technique will continue to be refined and improved, offering more opportunities for its use in monitoring response to therapeutics, obtaining follow-up evaluations, and performing research in EoE.

Figure 4:
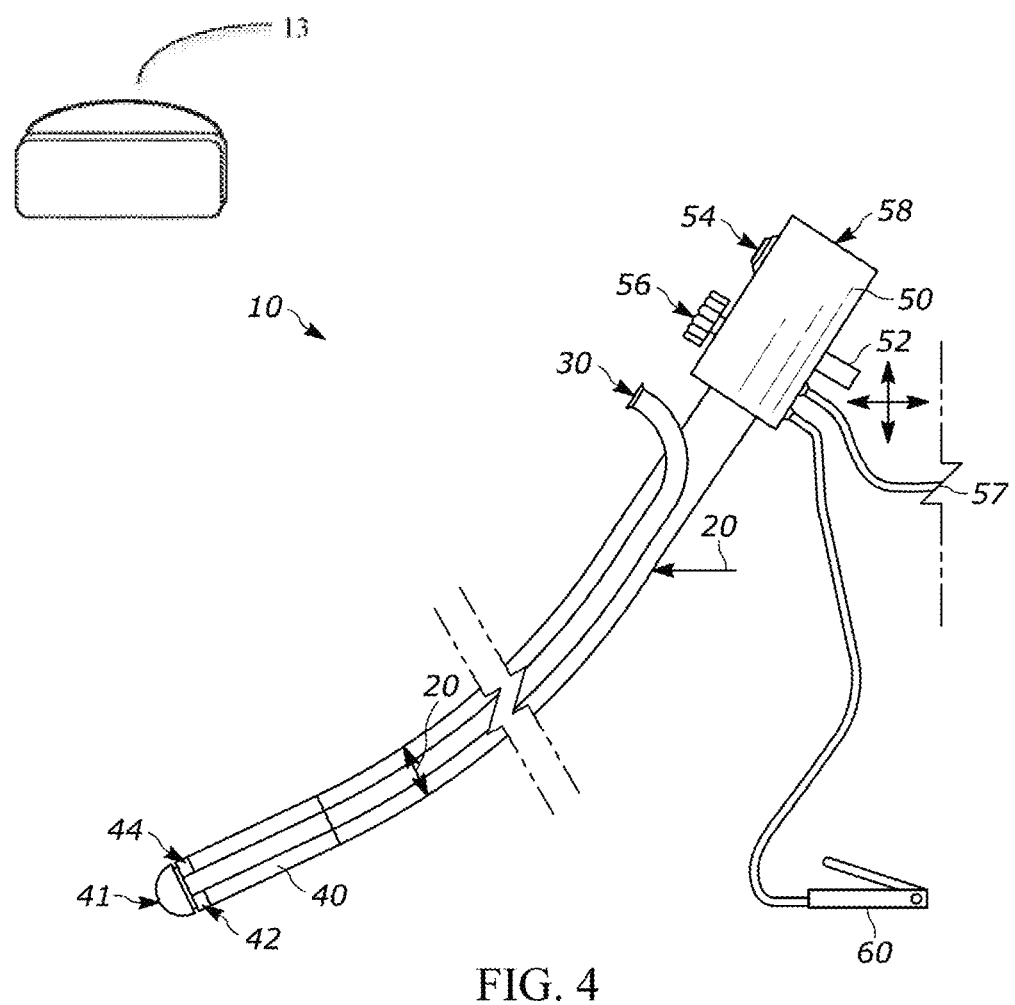
FIG. 4 is a drawing depicting a pediatric nasal endoscope according to aspects of the present invention.

Turning to FIG. 4, a pediatric nasal endoscope 10 was developed to perform TNE in children. The pediatric nasal endoscope 10 includes a flexible endoscope shaft 20 constructed from medical-grade slippery (such as a hydrophobic) material with a slick coating having a length of about 1.05 meters and a width of about 3.5 mm. The flexible endoscope shaft 20 has a biopsy channel 30 running the length of the endoscope shaft and is adapted to slidingly receive a pediatric nasal endoscope biopsy forceps 70 (See FIG. 5) within the lumen of the channel or allow suction or irrigation. 30. The distal end 40 of the flexible endoscope shaft 20 is rounded and can be flat or if the end user wishes designed to be terminated with an optional, removable soft silicone tip 41. The distal end 40 of the flexible endoscope shaft 20 also includes a high lumen LED 42 to provide light at the tip and a high-resolution video capture device to capture images or video in the region of the distal end 40 of the flexible endoscope 20. The proximal end 50 of the flexible endoscope shaft 20 can include a single 4-way tip deflection control lever 52 to control the displacement of the endoscope's tip, a button 54 to actuate photo or video capabilities of the endoscope, a hand control 56 to operate air and/or water suction, a line out 57 to a imaging system such as a computer monitor, an optional scope stiffening device 58 to allow its use in aerodigestive medicine. A foot pedal 60 can also be coupled to the endoscope to activate and control water flow and air suction.

Figure 5:
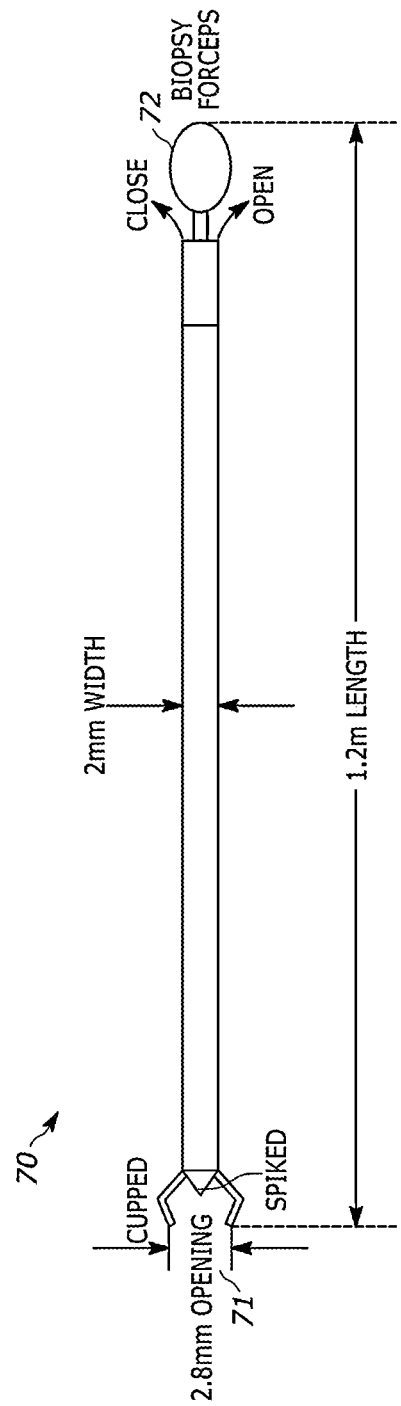
FIG. 5 is a drawing depicting a pediatric nasal endoscope biopsy forceps according to aspects of the present invention.

As discussed above, the flexible endoscope shaft 20 has a biopsy channel 30 running the length of the endoscope and is adapted to slidingly receive a pediatric nasal endoscope biopsy forceps 70 (See FIG. 5) within the lumen of the channel 30. Turning to FIG. 5, an exemplary pediatric nasal endoscope biopsy forceps 70 is illustrated. The pediatric nasal endoscope biopsy forceps 70 has a length of about 1.2 meters, which is slightly longer than the length of the biopsy channel 30, a width of about 2 mm, and opposing ends forming a distal end 71 and a proximal end 72. The distal end 71 includes a cupped and spiked tip with an opening of about 2.8 mm to 5 mm when fully open. The proximal end 72 includes an actuator to open and close the tip at the distal end 71 of the forceps 70. Examples 1 & 2, presented below, document the development of the transnasal endoscopy/esophagoscopy (TNE) to assess the esophageal mucosa in children using the pediatric nasal endoscope.

Further embodiments of endoscopic devices, elements thereof, and/or systems utilizing endoscopes are described herein. Endoscopes may be used in combination with other elements in a system to enhance the capabilities of the scope and/or increase a number of uses for which the scope may be used.

Figure 6:
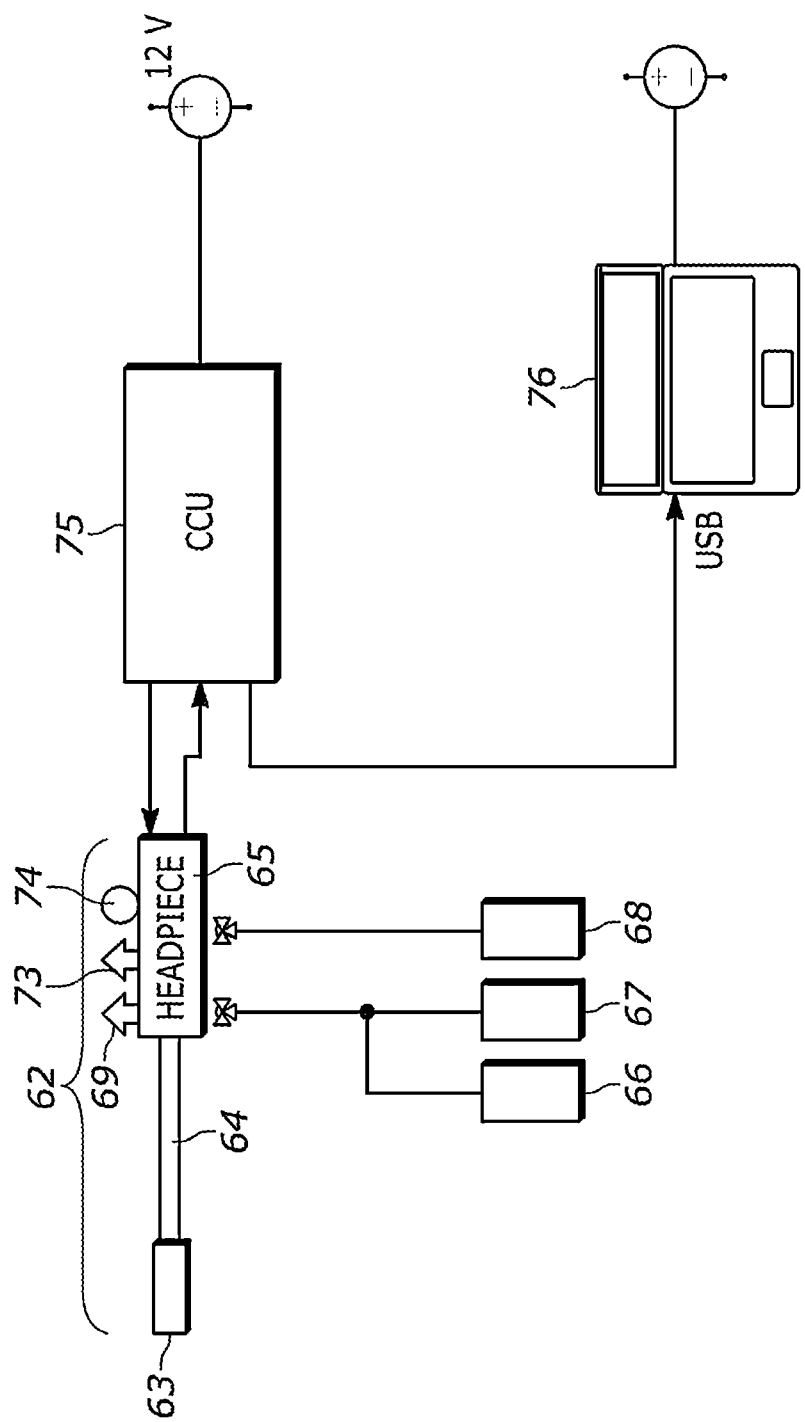
FIG. 6 is a block diagram depicting a system that incorporates an endoscope.

A system including endoscope 62 is shown in FIG. 6. As shown, endoscope 62 includes distal element 63, elongated element 64 and control element 65. An endoscope may be coupled to external supplies and/or reservoirs of materials. As shown in the illustrative example of FIG. 6, endoscope 62 is coupled to air supply 66, liquid supply 67, and suction 68. In addition, endoscope 62 includes interface elements 69, 73. Endoscope 62 is coupled to computer control unit 75 and computer 76.

The control element may include a port or a number of ports which are used to provide and/or removal materials to/from a target area. For example, ports may be used to supply and/or remove fluids to/from a target area, such as water, air, and/or medications in specific measured amounts. In some embodiments, an interface element may be configured to deliver one or more pre-determined amounts of water, air and/or medicine during use by the operator based on a procedure, protocol, patient needs (for example, patient size) and/or preferences of the operator. In alternate embodiments, an interface element may be configured to remove predetermined amounts of fluids.

In some instances, suction may connected to a port in order to provide suction to a target area. Ports may include coupling structures to couple various delivery systems to the control element.

Some embodiments of control elements may include interface elements. For example, an interface element may be used to control the positioning and/or functions of distal element, a portion of the elongated element, the function of devices and/or sensors positioned along the elongated element and/or the distal element. In particular embodiments, an interface element may be used to determine a distance from an insertion point and/or measure luminal body findings. For example, determining a diameter of lumen, such as an esophagus or bronchus, and/or measuring the size a lumen and/or findings therein, such as a gastric polyp or ulcer. For example, interface elements may control aspects of the optical system. In some embodiments, interface elements may control image capture, video, and/or audio recording.

For example, as depicted in FIG. 6, interface element 69 may control the imaging element. In particular, in some instances, an interface element may be programmed such that different user interactions may be recognized by the system as different commands. In particular, interface element 69 may be programmed to capture an image upon a momentary touch. In contrast, interface element 69 may be programmed to start and/or end video capture when interface element is pressed and held. Further, interface element 73 may be programed such that a touch, for example, a momentary touch, may provide an instruction that the device will auto-populate a section of a report, while a press and hold motion will instruct the device to record audio. For example, the auto-populate feature would enable audio to be transmitted from the microphone in the control element to a reporting system where it would be transcribed into a report system automatically.

In some embodiments, an auto-populate feature may be used to populate any portion of form with transcribed audio data, audio files, video files, metrics measured by sensors, in particular, dimensions, position of the endoscope, and/or other physiological conditions within a body or portion of the body being viewed.

A control element may include a steering mechanism. For example, FIG. 6 depicts user interface 74 which may be used as a steering mechanism. In some embodiments, the steering mechanism will be a four-way mechanism. For example, the steering mechanism may be constructed along the lines of a joystick and/or roller ball to allow for single hand manipulation and steering.

The control element may have a housing constructed using standard methods known in the art, as well as newly developed technologies. For example, the control element may have a housing that is constructed using three dimensional printing.

Figure 7A:
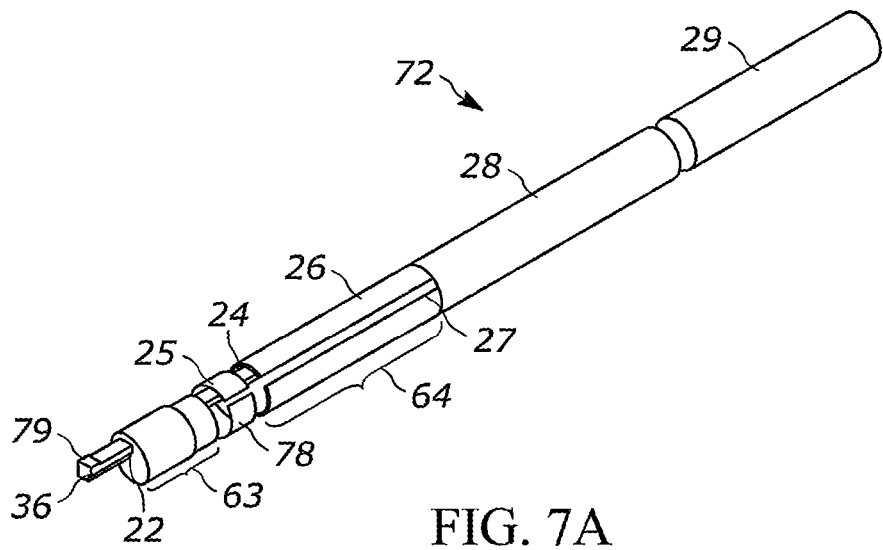
FIG. 7A is an exploded view of an illustrative example of the distal and elongated elements of an endoscope.
Figure 7B:
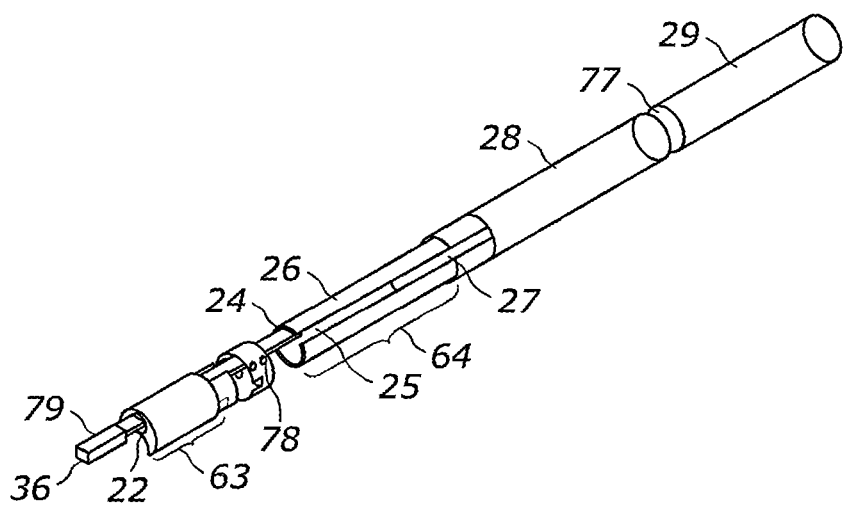
FIG. 7B is an exploded view of an illustrative example of the distal and elongated elements of an endoscope.

FIGS. 7A-B depict an exploded partial cut-away views of endoscopes 77. In particular, as shown in FIG. 7A, distal element 63 is positioned proximate steering collar 78 which is positioned proximate to elongated element 64. As shown, a portion of imaging element 79 extends from the distal element while a portion is positioned in conduit 22 of distal element 63 and extends through steering collar 78 and into conduit 24 of the elongated element 77

The distal element of the endoscope may have a rounded end, a flat end, and/or a combination. In some embodiments, an end of the distal element may include a soft tip, for example, a soft silicone tip.

Various embodiments of an end view of a distal element are depicted in FIGS. 7A, 7B, 8, 11, 15, 18, 22, 26, 29. Distal elements may be constructed from one or more materials including, but not limited to plastics such as acrylonitrile butadiene styrene (ABS), polycarbonate (PC), polycarbonate-acrylonitrile butadiene styrene (PC/ABS), high density polyethylene (HDPE), polyamide (PA), polyether ether ketone (PEEK), polypropylene (PP), and/or polyvinyl chloride (PVC), metals such as aluminum, stainless steel, carbon steel, titanium, and/or magnesium and/or combinations thereof. The materials depicted in these various embodiments may be combined based on the needs of the use. An illustrative example of the distal element includes stainless steel.

Elongated elements 77 of FIGS. 7A-B, include steering collar 78, extruded element 26, tubular element 28 and shrink element 29. As is shown in FIGS. 7A-B, extruded element is surrounded at least in part by tubular element 28, which is in turn surrounded by the shrink element 29. As can be seen in both FIGS. 7A-B, steering guides 25 are positioned within groove 27 on the extruded element 26. FIG. 7A depicts steering guides connected to the steering collar 78 at groove 27.

Figure 8:
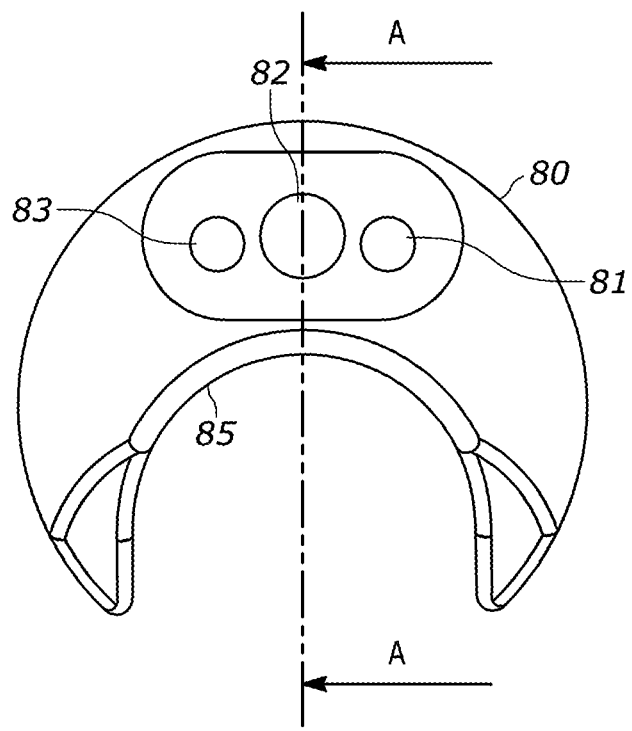
FIG. 8 is a drawing depicting an end view of an illustrative example of a distal element for an endoscope.

As shown in FIG. 8, an end of distal element 80 shows multiple conduits 82, 83, 84. In an embodiment, conduits 82, 83, 84 may be used to house devices and/or portions thereof that are necessary for the functioning of the endoscope. In particular embodiments, one or more of the conduits may be used to house optical fiber. Depending on the design of the endoscope and positioning of various elements therein the conduits may extend from the distal end to the proximal end of the elongated element. In alternate embodiments, one or more of the conduits may extent from a middle of the elongated element to an end. For example, if a illumination source is positioned at point corresponding to a middle of the elongated element, a conduit that houses the optical fiber to provide light to the distal element may run from the distal element to the position of the illumination source located at the middle of the elongated element.

Figure 9:
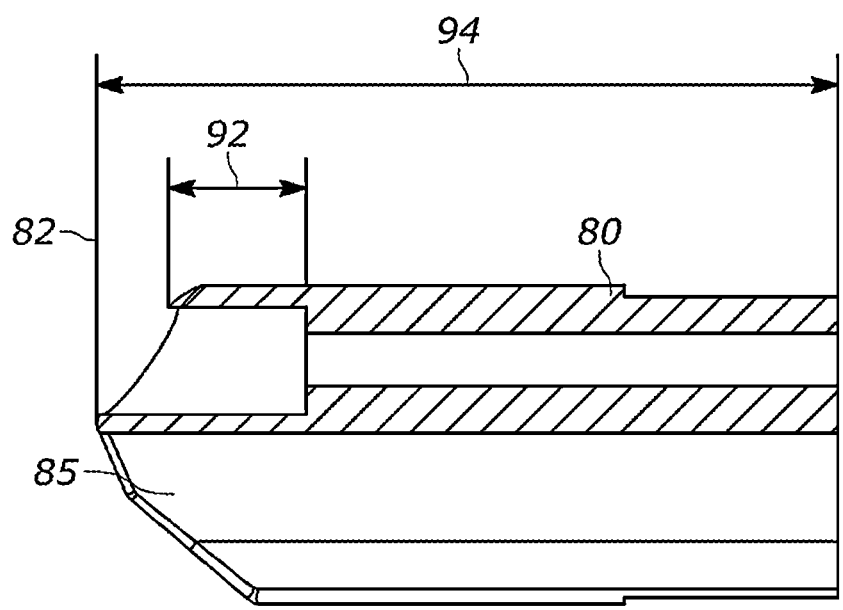
FIG. 9 is a drawing depicting a cross-sectional view of an illustrative example of a distal element for an endoscope.

Distal element 80 includes channel 85. As shown in FIG. 8, channel 85 may be partially open. FIG. 9 depicts a cross-sectional view of FIG. 8 along line A-A. As shown in FIG. 9, distal element 80 includes conduit 82 and channel 85 both of which extend along the length of distal element 80. As can be seen, a geometry of conduit 82 may vary along a length of the distal element. For example, an inner diameter can be varied. An outer diameter of distal element may also vary. For example, as can be seen in FIG. 9 such that it may be fitted to an elongated element. As can be seen in FIG. 9, a face of the distal element 80 is shaped.

Figure 10:
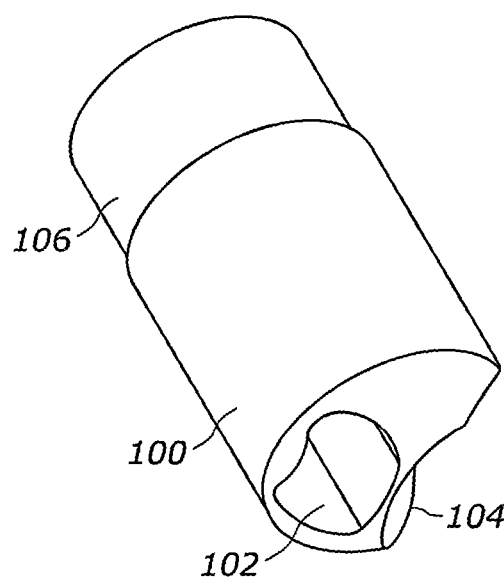
FIG. 10 is a drawing depicting a perspective view of an illustrative example of a distal element for an endoscope.

FIG. 10 depicts a perspective view of an embodiment of a distal element having a single conduit 102 and an open channel 104. Further, it can be seen in FIG. 10, that the outer diameter of the distal element 100 varies its length. Coupling section 106 has a smaller diameter than the rest of distal element. The coupling section may be constructed in a manner such that it couples to an elongated element.

Figure 11:
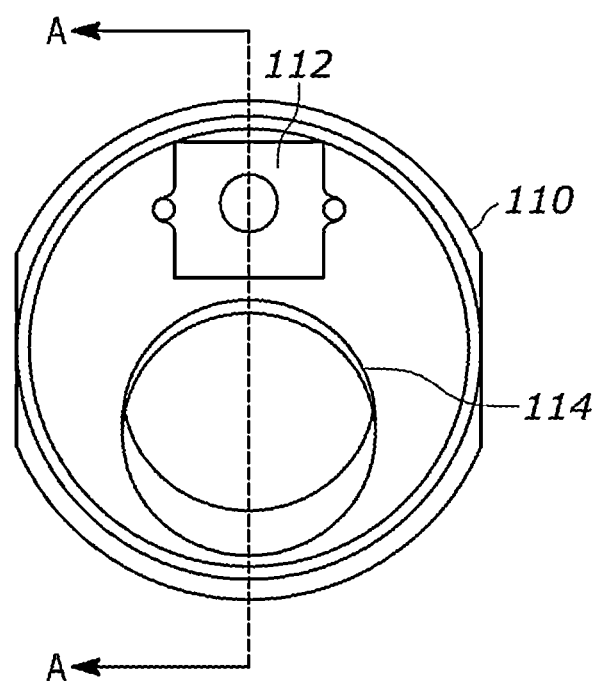
FIG. 11 is a drawing depicting an end view of an illustrative example of a distal element for an endoscope.
Figure 12:
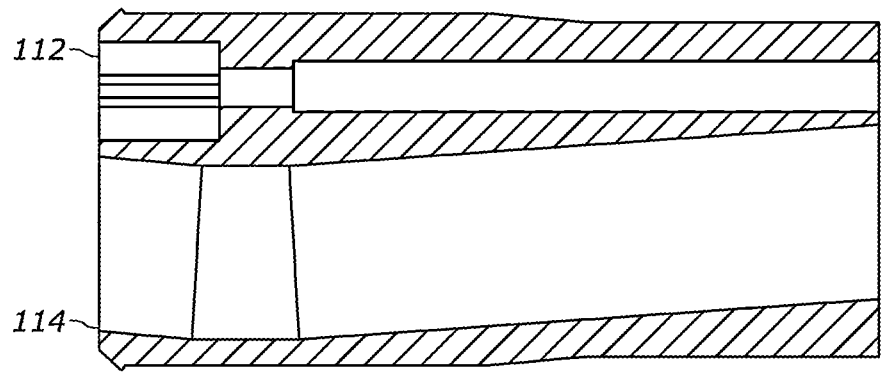
FIG. 12 is a drawing depicting a cross-sectional view of an illustrative example of a distal element for an endoscope.

FIG. 11 depicts an end of distal element 110 having multiple conduits 112, 114. Conduit 114 is cut using a swept cut path. FIG. 12 depicts a cross-sectional view of distal element 110. As can be seen in FIG. 12, a path of conduit 114 varies along a length of the distal element. In particular, the path of conduit 114 moves from an edge of the distal element 110 toward a middle of the distal element 110. A geometry of conduit 112 changes along a length of distal element 110. As can be seen in FIG. 12, a section of conduit 112 has a rectangular geometry and a further section of conduit 112 has a substantially circular geometry. As shown in FIG. 12, an outer diameter of the distal element 110 varies along the length of the distal element.

Figure 13:
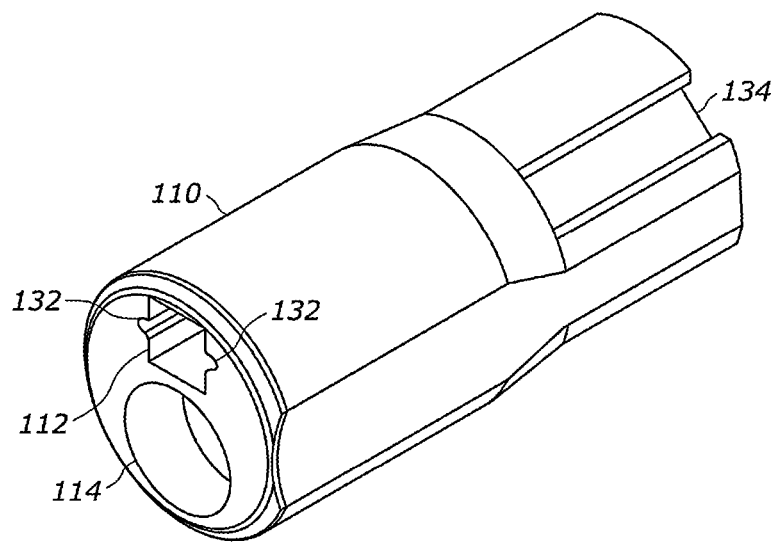
FIG. 13 is a drawing depicting a perspective view of an illustrative example of a distal element for an endoscope.
Figure 14:
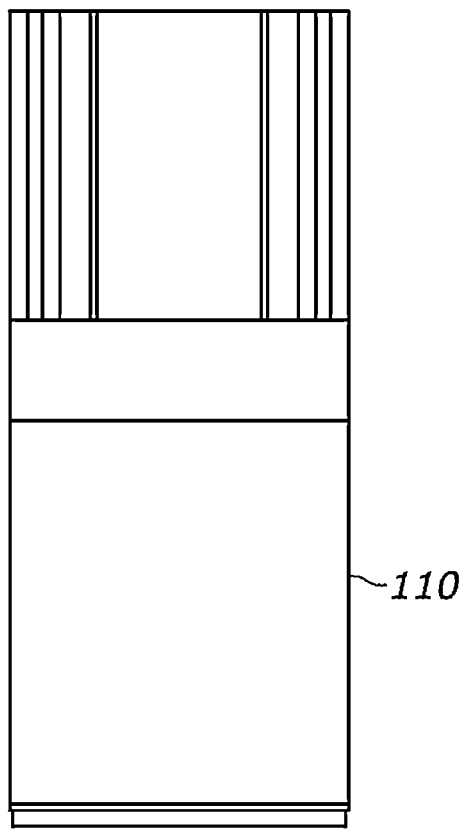
FIG. 14 is a drawing depicting a top view of an illustrative example of a distal element for an endoscope.

FIG. 13 depicts a perspective view of distal element 110 shown in FIGS. 11, 12, 14. As can be seen in FIG. 13, conduit 112 includes cut-outs 132. Cut-outs may conform a shape of devices, tubing, and/or other elements. In some instances, cut-outs may help to elements placed within a conduit. As shown in FIG. 13, an outer diameter and geometry is varied along the length of the distal element 110.

Cut-out 134 is positioned on an outer surface of distal element 110. In some embodiments, cut-out 134 may be designed to couple with an elongated element.

An embodiment may include a cut-out designed to house a device such as a sensor, imaging element, light, or the like, cable, wire, and/or fiber optic element. FIG. 14 depicts a top perspective view of distal element 110. From this view, the variation of the geometry along the length of the distal element is visible.

Figure 15:
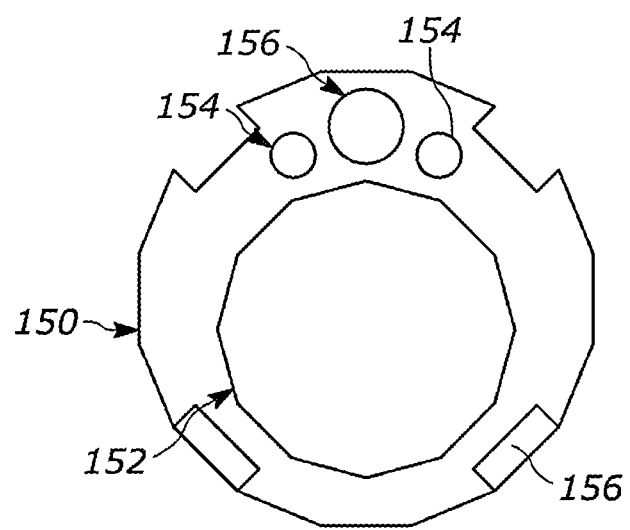
FIG. 15 is a drawing depicting an end view of an illustrative example of a distal element for an endoscope.

As shown in FIG. 15, distal element 150 includes multiple conduits 152, 154, 156 and channels 156. Conduit 152 has a larger diameter that the remaining conduits. Conduit 152 may act as a working conduit. Channels 156 are partially open. In some embodiments, channels that are partially open may house a camera sensor and/or optical fiber.

FIGS. 16-19 depict various views of a distal element constructed using sliced layers. Sliced layer construction may allow for more complicated geometries. Processing limitations of standard construction methods may limit design given size ranges of these elements, thus, it may be desirable to used sliced layer construction and/or additive manufacturing, such as three dimensional printing. For example, a sliced layer construction process may enable the use of a swept cut path in a conduit of the distal element.

Figure 16:
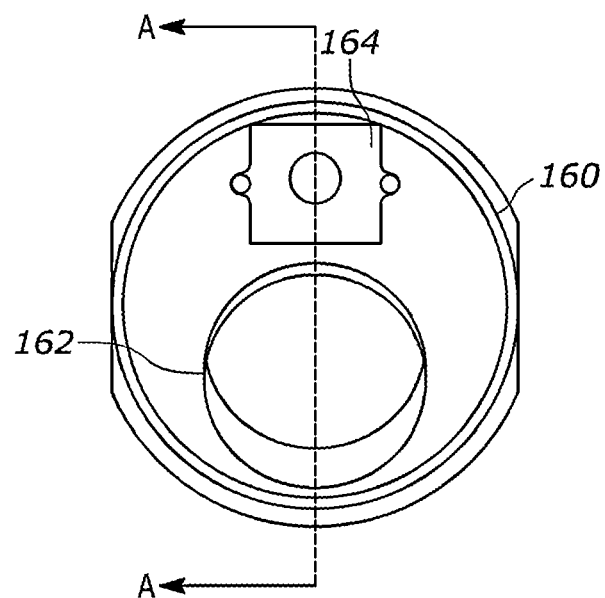
FIG. 16 is a drawing depicting an end view of an illustrative example of a distal element for an endoscope.
Figure 17:
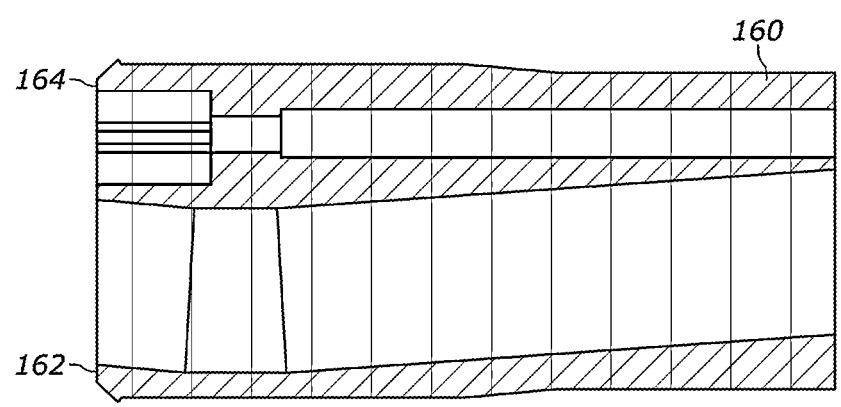
FIG. 17 is a drawing depicting a cross-sectional view of an illustrative example of a distal element for an endoscope.
Figure 18:
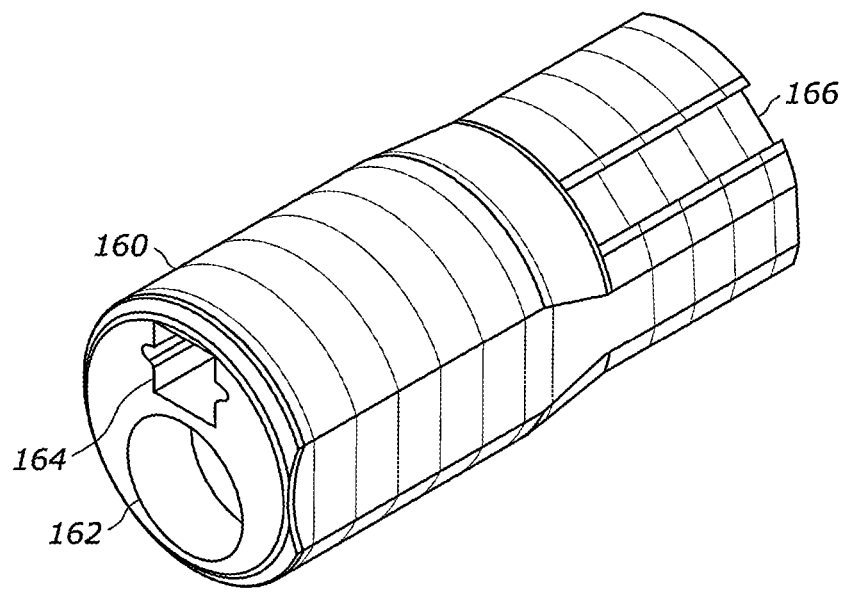
FIG. 18 is a drawing depicting a perspective view of an illustrative example of a distal element for an endoscope.
Figure 19:
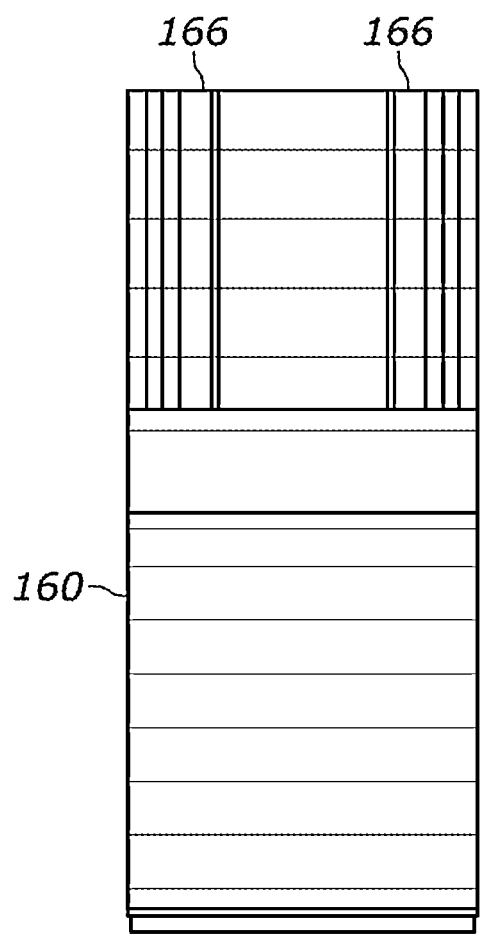
FIG. 19 is a drawing depicting a top view of an illustrative example of a distal element for an endoscope.

As shown in FIGS. 16-17, the sliced layers allow for changing an elevation of conduit 162 along the length of the distal element. Conduit 164 varies in geometry along a length of the distal element 160. FIG. 18 depicts a perspective view of distal element 160. Distal element includes conduits 162, 164, as well as channels 166.

Figure 20:
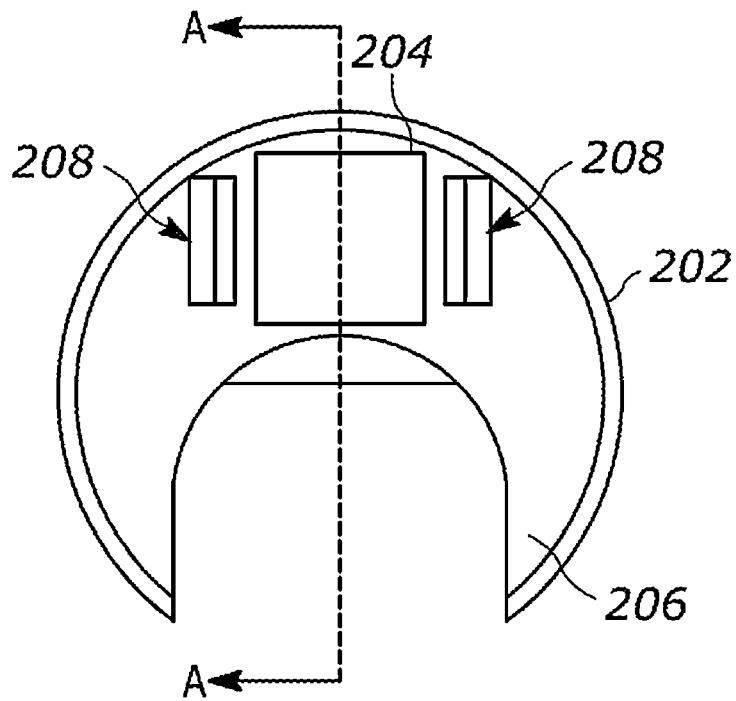
FIG. 20. is a drawing depicting an end view of an illustrative example of a distal element for an endoscope.
Figure 21:
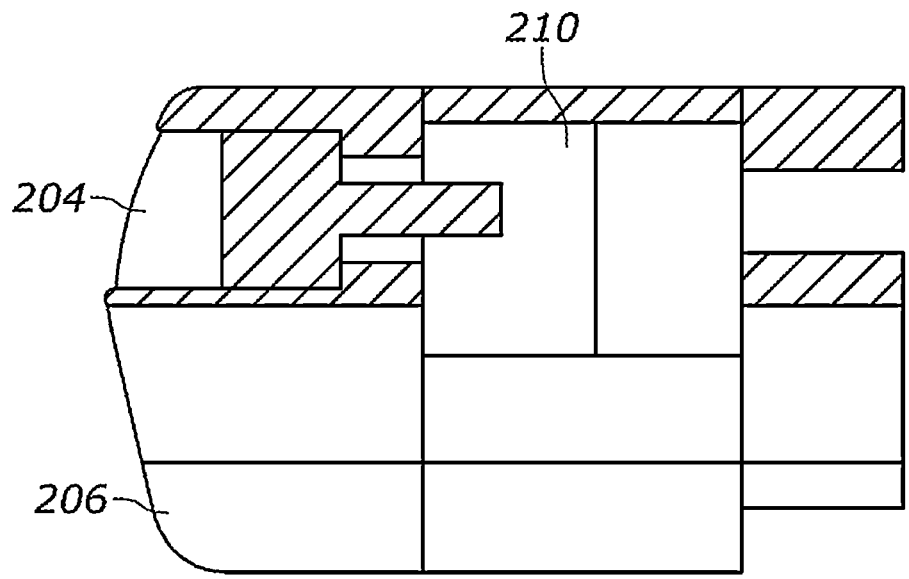
FIG. 21 is a drawing depicting a cross-sectional view of an illustrative example of a distal element for an endoscope.
Figure 22:
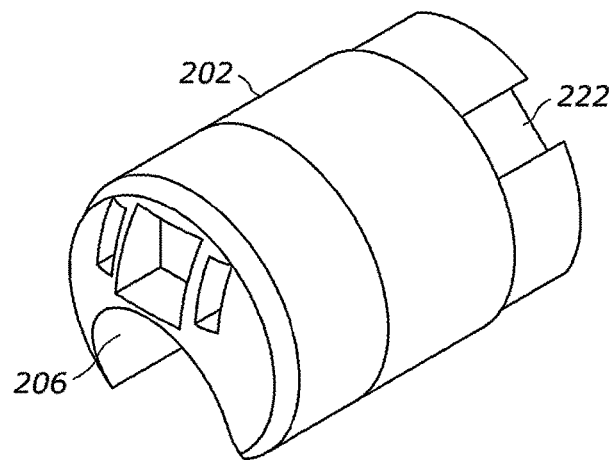
FIG. 22 is a drawing depicting a perspective view of an illustrative example of a distal element for an endoscope.
Figure 23:
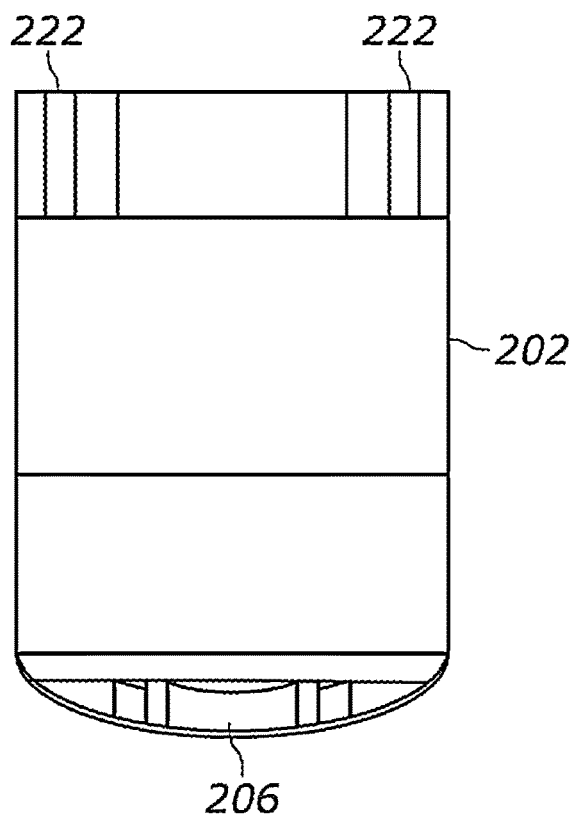
FIG. 23 is a drawing depicting a top view of an illustrative example of a distal element for an endoscope.

As illustrated in FIGS. 20-23, distal element 202 is constructed from multiple sections. Use of multiple sections in the distal element may inhibit undercuts. Distal element 202 includes conduit 204, as well as open channel 206. As depicted in FIG. 20 showing an end view of distal element 202 which includes channels 208 for lighting elements such as a lightpipe, fiber optic elements, or clear epoxy. FIG. 21 depicts a cross-sectional view of distal element 202 shown in FIG. 20 along line A-A. Light source 210 is positioned proximate conduit 204 such that the light source provides light to a target area through channels 208. Light source may include, but is not limited to Xenon lights, organic light-emitting diode ("OLED") lights, light-emitting diode ("LED") lights, for example, high lumen LEDs. FIGS. 22-23 show channels 222 positioned on an outer surface of the distal element 202.

Figure 24:
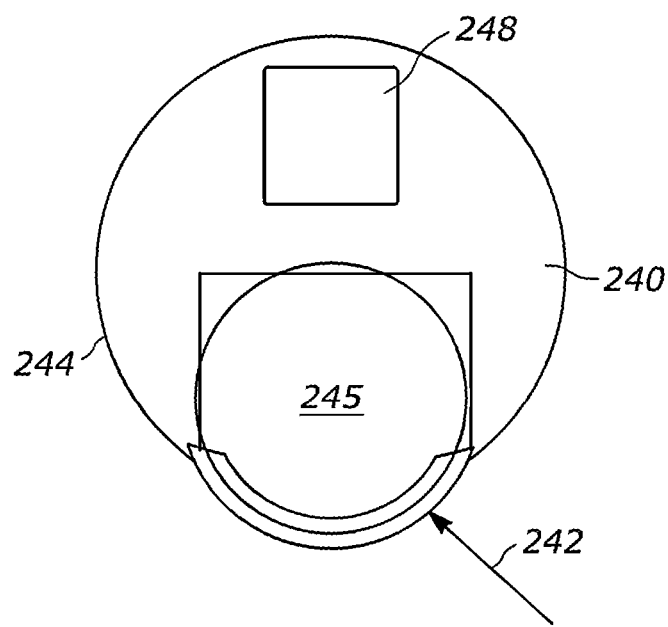
FIG. 24 is a drawing depicting an end view of an illustrative example of a distal element for an endoscope.
Figure 25:
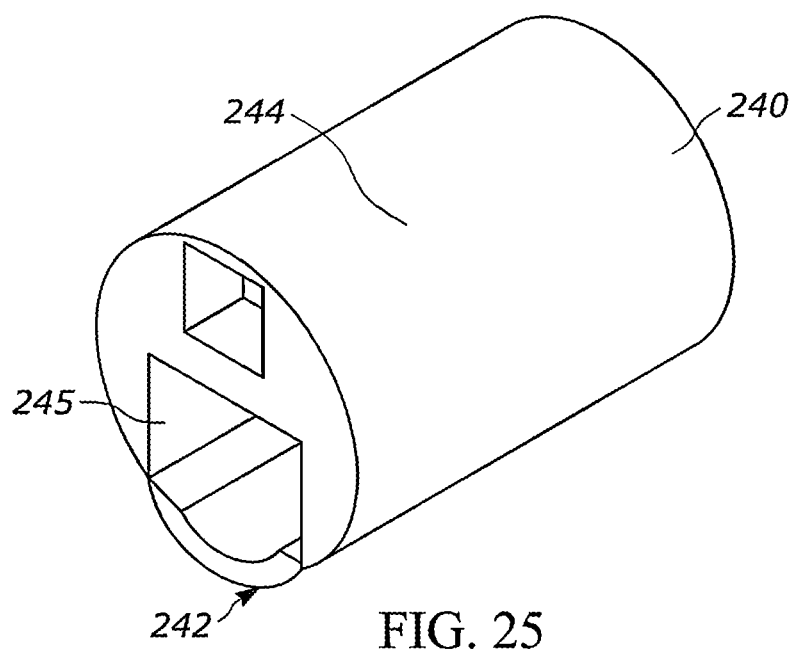
FIG. 25 is a drawing depicting a perspective view of an illustrative example of a distal element for an endoscope.
Figure 26:
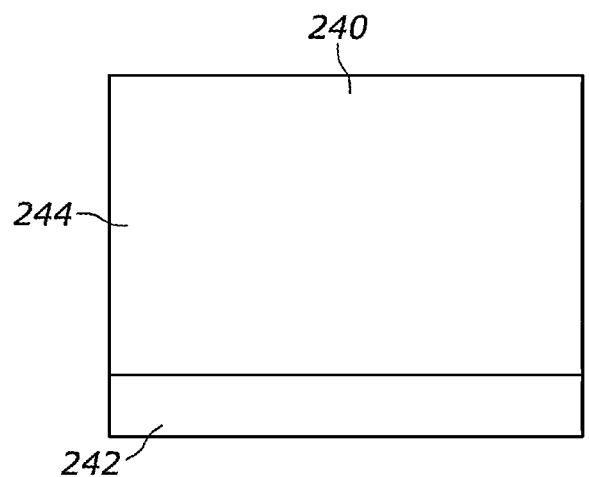
FIG. 26 is a drawing depicting a side view of an illustrative example of a distal element for an endoscope.

FIG. 24 depicts an end view of distal element 240 constructed from flexible member 242 and rigid body 244 which define conduit 245. Conduit 248 is depicted clearly in FIG. 25 which shows a perspective view of the distal element. A side view of the distal element 240 is shown in FIG. 26.

Figure 27:
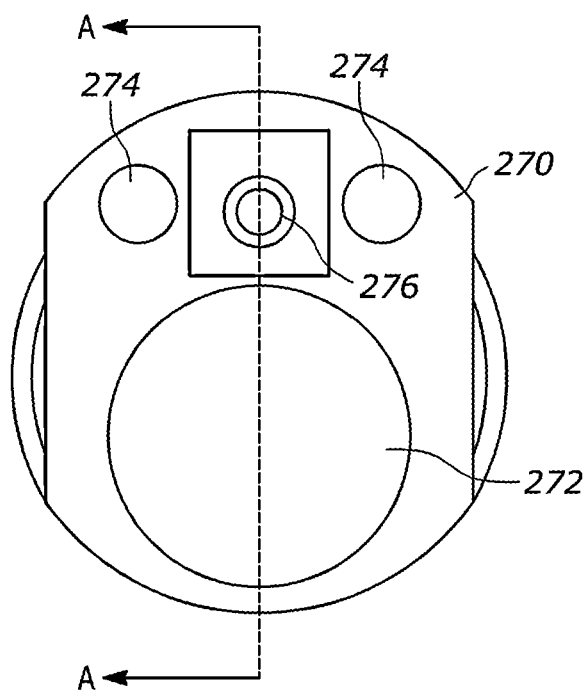
FIG. 27 is a drawing depicting an end view of an illustrative example of a distal element for an endoscope.
Figure 28:
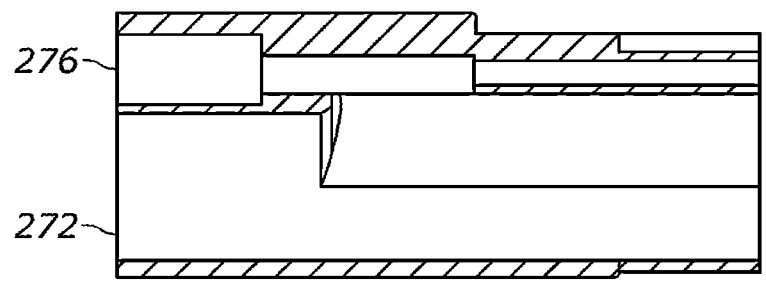
FIG. 28 is a drawing depicting a cross-sectional view of an illustrative example of a distal element for an endoscope.

FIG. 27 illustrates an end view of a distal element having an egg shaped face. Distal element 270 includes conduits 272, 274, 276. A cross-sectional view of FIG. 27 along line A-A is shown in FIG. 28. Conduits 272, 276 are both shown having varying diameters along the length of the distal element. Conduit 272 may be a working conduit or working channel. In an embodiment, conduit 276 may house an optical sensor.

Figure 29:
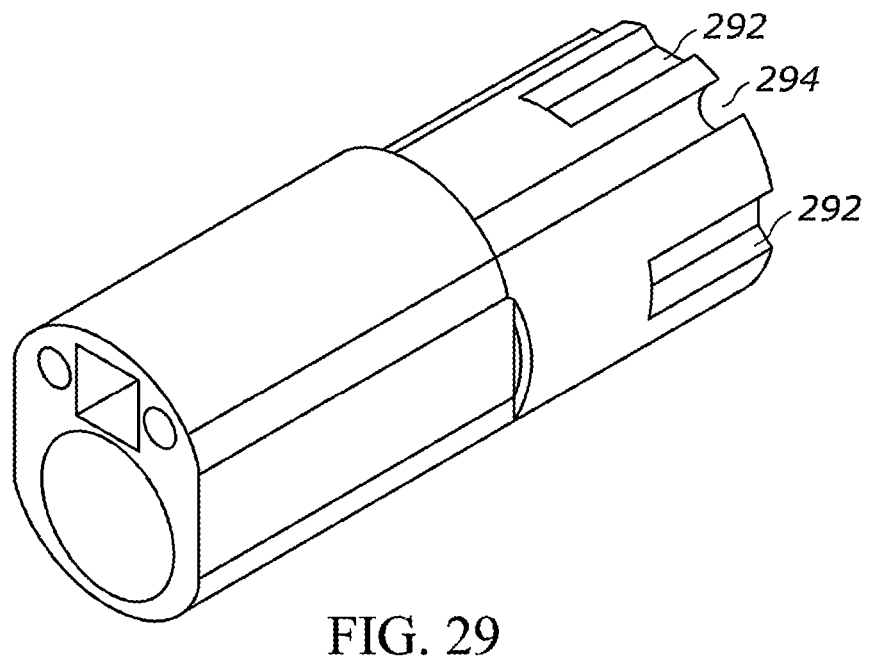
FIG. 29 is a drawing depicting a perspective view of an illustrative example of a distal element for an endoscope.
Figure 30:
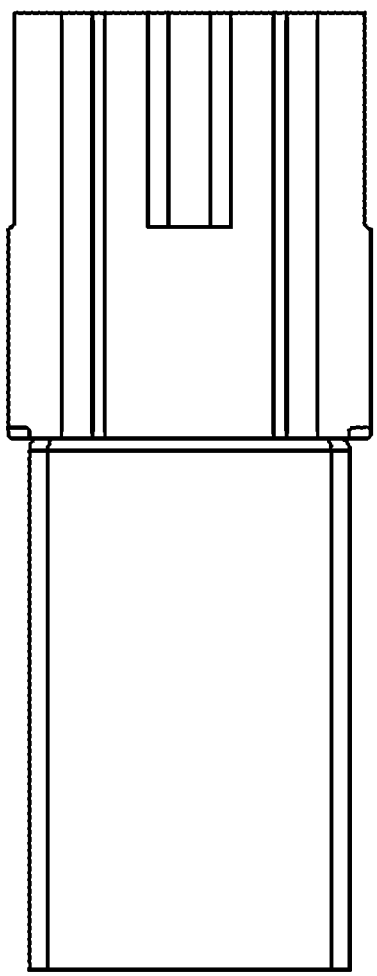
FIG. 30 is a drawing depicting a top view of an illustrative example of a distal element for an endoscope.

FIGS. 29-30 depict a perspective view and a top view of distal element 270, respectively. Channels 292, 294 are positioned on an outer surface of distal element 270. FIG. 30 clearly depicts the varying outer diameter along the length of the distal element.

Figure 31:
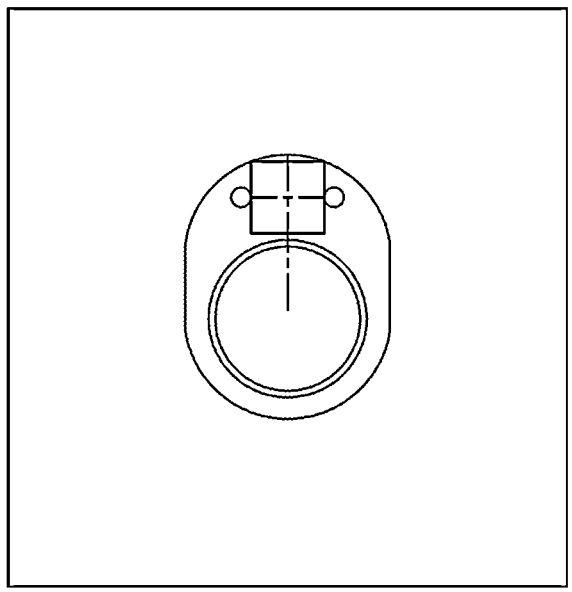
FIG. 31 is a drawing depicting an end view of an illustrative example of an overmold for a distal element for an endoscope.
Figure 32:
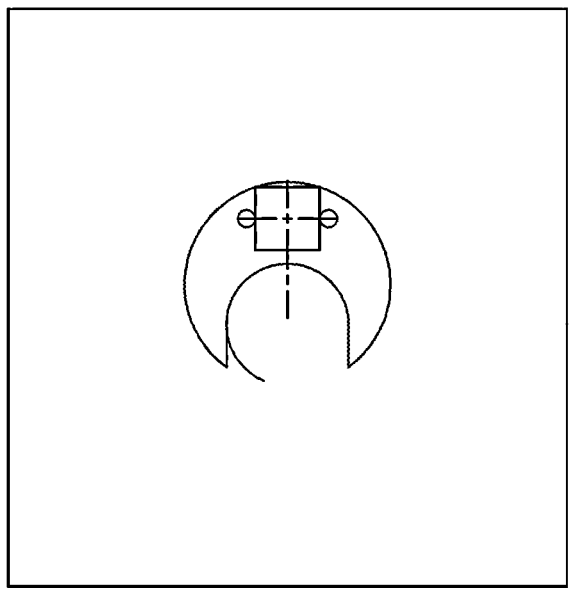
FIG. 32 is a drawing depicting an end view of an illustrative example of an overmold for a distal element for an endoscope.
Figure 33:
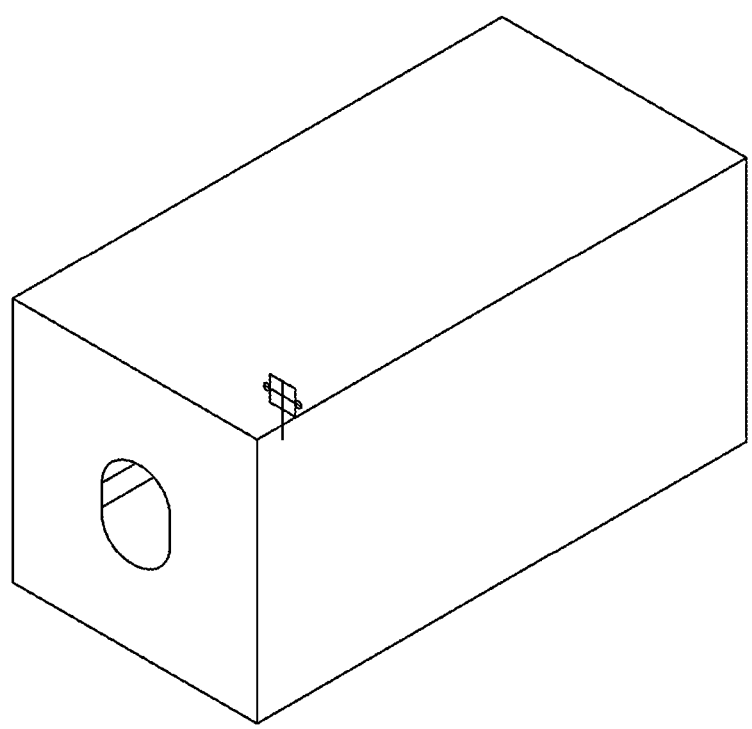
FIG. 33 is a drawing depicting an end view of an illustrative example of an overmold for a distal element for an endoscope.

Overmold drawings reflect a tool necessary to create the distal element. Various configurations were constructed that corresponded to the geometries of the distal element as can be seen in FIGS. 31-33.

As shown in FIG. 9, distal element 80 includes conduit 82 and channel 85 both of which extend along the length of distal element 80. As can be seen, a geometry of conduit 82 may vary along a length of the distal element. For example, an inner diameter can be varied. An outer diameter of distal element may also vary. For example, as can be seen in FIG. 9 such that it may be fitted to an elongated element. As can be seen in FIG. 9, a face of the distal element 80 is shaped.

The scope may include a distal element having openings for additional devices or elements. For example, the distal element may include openings for an illumination element, such as a fiber optic cable, light, and/or light source, and/or an optical element, such as a camera.

An optical element may include a device having a field of view of greater than 60°. In some embodiments, the field of view of the optical element may be greater than 85° or as high as 150 degrees. Further, the depth of field may be as small as 5 mm greater than 15 mm. In some instances, the depth of field may be greater than 19 mm. An optical element such as a camera, for example, a high definition camera or videoscope may include devices such as, but not limited to miniature videoscopes.

The distal element may also include openings which may allow for manipulation at a predetermined location, delivery of materials, such as air, liquid, medicines, devices, etc., and/or retrieval of materials, such as tissue, devices, fluids. In an embodiment, the distal element may include an opening which allows for use of suction at a predetermined location and/or a target area.

Elongated elements may couple to both the distal element and the control element. A length of length of an elongated element may be in a range between 0.5 to 1.5 meters. For example, an elongated element may have a length in a range from about 0.8 to 1.2 meters in some embodiments. An outer diameter of an elongated element may be less than about 4.5 millimeter. In some embodiments, the outer diameter of an elongated member may be less than 4.0 millimeter. For example, an elongated element may have an outer diameter of less than about 3.5 millimeters in an embodiment.

A stiffness of the elongated element may vary along its length. At least a portion of the length may be flexible. In some embodiments, variable stiffness along the length of the elongated element may be created using a stainless steel tube that is laser cut with a variable interrupted spiral pattern. The more cuts, the more material is removed and the more flexible the shaft becomes. Thus, an elongated element may be designed to have a stiffer area proximate the control element such that torque cam be transferred, while being flexible proximate the distal element such that tight bends can be negotiated and/or patient comfort improved. In an alternate embodiment, the elongated element may include a braided metal section to provide variable stiffness.

In some embodiments, a length of a flexible portion of the elongated element may be in a range from about 30 to about 50 millimeters. For example, a flexible portion of an elongated member may have a length in range from about 35 to 45 millimeters. In an embodiment, the length of the flexible portion of the elongated element may be approximately 40 mm.

An elongated element may include one or more conduits. The conduits may have various configurations. For example, the conduits may be coaxial, positioned proximate each other, and/or positioned on opposite sides of the cross-section of the elongated element. Conduits may include one or more lumen. For example, a conduit may be a multi-lumen.

Conduits may act as a housing for elements inserted into the elongated element. In some embodiments the elongated element may have one or more conduits configured to receive devices and/or sensors to provide access to a target area.

In some embodiments, conduits may provide a path for materials to reach the distal element and/or a target area. Further, a conduit may be used to transport materials from the target area to control element or, in some cases, to a position external to the control element.

Elongated element 62 includes conduit 24 running the length of the endoscope elongated element. In some instances, the conduit may slidingly receive instruments, such as a nasal endoscope biopsy forceps 70 (See FIG. 5) within the lumen of the conduit and/or allow suction or irrigation.

A working conduit in the elongated element may have an inner diameter of greater than about 2.0 millimeters. Further, the inner diameter of working conduit may be greater than about 2.1 millimeters in some embodiments.

At least one conduit through the elongated element may have an inner diameter of greater than about 1.3 millimeters. Some embodiments may include conduits having an inner diameter of about 1.4 millimeters or greater.

A sensor array may be used to take measurements throughout a procedure. For example, a sensor array may make distance measurements, for example, the distance that an endoscope has traveled in the body, luminal measurements, such as diameters, lengths, and/or volumes, quantitative changes, physiological measurements within the body, such as temperature, pulse oximetry measurements, and/or etc.

An endoscope may include an elongated element having a flexible section. This flexible section of the elongated element may be constructed from a medical-grade material. In particular, a hydrophobic material may be used. Hydrophobic materials may create a slippery surface which allows the device to be inserted with more ease and/or less discomfort to the patient.

Elongated member 62 of endoscope also includes imaging element 79 and illumination element 36. For example, a high lumen LED may be used to provide light and a high-resolution video capture device may be used to capture images and/or video in the region of the distal end of the endoscope.

As shown in FIGS. 6 and 34-42, control elements may include any combination of ports, interface elements, and/or indicators. In some instances, an interface element may include a steering element which may control the movement and/or displacement of the distal element and/or optical element of the endoscope. For example, the degrees of deflection from the normal position for the distal element may be greater than 90° in at least one direction. For example, the degrees of deflection from the normal position for the distal element may be 90° in three directions and greater than 90° in a fourth direction. Deflection may be achieved by pulling on steering guides, for example, steering wires.

Interface elements may be positioned on a control element to provide for ease of use of the operator. For example, in some embodiments, interface elements may be positioned along a top surface, a side surface, and/or an underside of the control element. An embodiment of an interface element may act in a joystick-like manner to control movement of the distal element.

Figure 34:
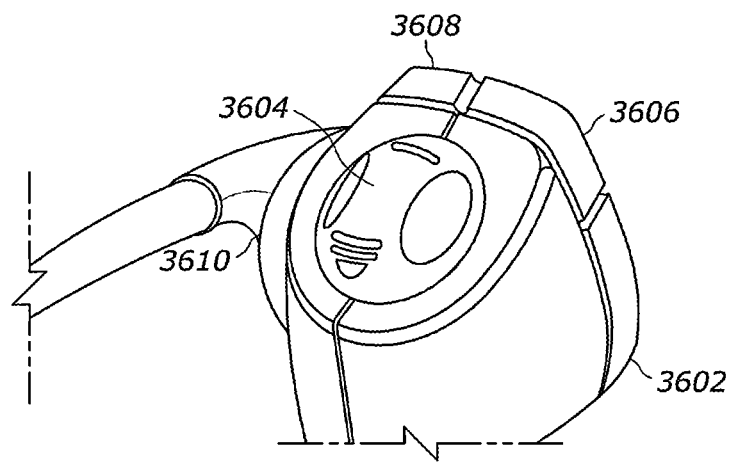
FIG. 34 is a drawing depicting a top perspective view of an illustrative example of a control element for an endoscope.

FIG. 34 depicts a control element 3602 which is designed such that it conforms to the shape of a hand. Interface element 3604 is controlled in a manner similar to a roller ball for ease of use. Further, interface elements 3606, 3608, may be control audio recording and image capture, respectively. In some embodiments, interface element 3606 may control audio recording and transcription. These interface elements may have multiple settings. For example, a quick press may take an image or record a predetermined amount of audio, while pressing and holding these elements may activate video recording or extended audio recording. Further, the interface elements may be programmed to initiate auto-reporting data to one or more reports, databases, or processors. Data may include, for example, audio, visual, positioning, and temporal data, as well as physical and physiological measurements.

Figure 35:
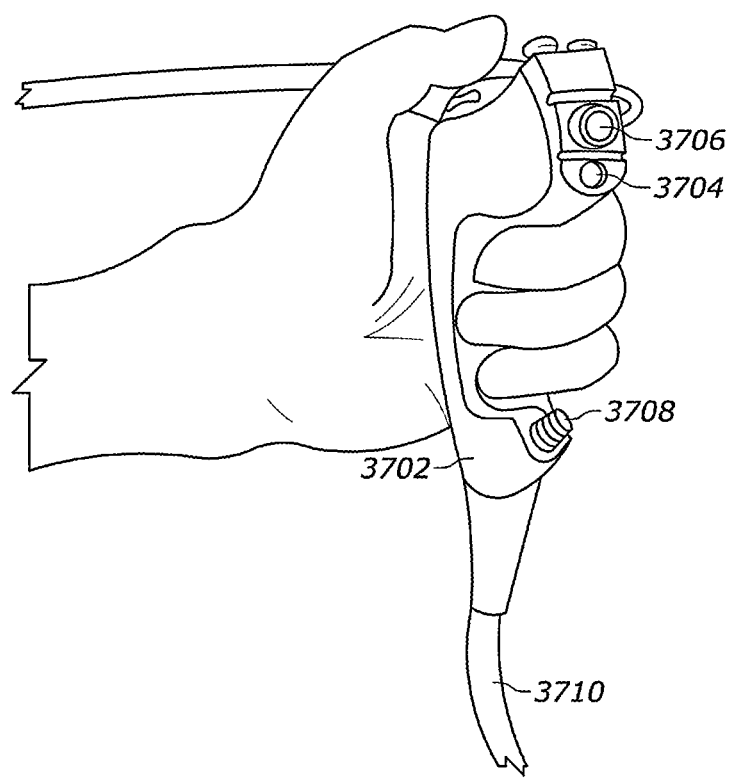
FIG. 35 is a drawing depicting a front perspective view of an illustrative example of a control element for an endoscope.

In some instances, the functionality of the interface elements may be programmable by a user for ease of use. In alternate embodiments, the functionality of the interface elements may be defined by a use of the device. For example, when then endoscope device is used to monitor a feeding tube the needs may be different from when the endoscope device is used to conduct a TNE. FIG. 35 depicts a front perspective view of control element 3702 which conforms to the shape of a hand. As can be seen in FIG. 35, ports 3704, 3706 may be positioned such that they do not interfere with the interface elements and the user's ability to control aspects of the endoscope. For example, port 3704 serves as a connection point for suction while port 3706 allows for a connection of fluids, in particular, air and/or water. Port 3708 provides access to a conduit and/or channel that runs through elongated element 3710.

In some embodiments, the control element may include multiple ports. At least one port may provide access to a channel and/or conduit within the elongate member. An insertion element, for example an instrument may be inserted into a conduit of the elongated element using a port. Further, an instrument may be coupled to a control element at a port which provides access to a conduit and/or channel within elongated element. An insertion element may include, but is not limited to an instrument, such as forceps, in particular, biopsy forceps, a feeding tube, a cable for sensors, sensors, accessory, illumination elements and/or optical elements. Further, interface elements may be positioned on a control element such that it provides easy maneuverability of the distal element.

In some embodiments, after positioning of an instrument within the elongated element, the control element may be removed. Wires and/or connectors to various elements, for example, audio and imaging elements, sensors, and the like may be remain so that these elements can be used.

Figure 36:
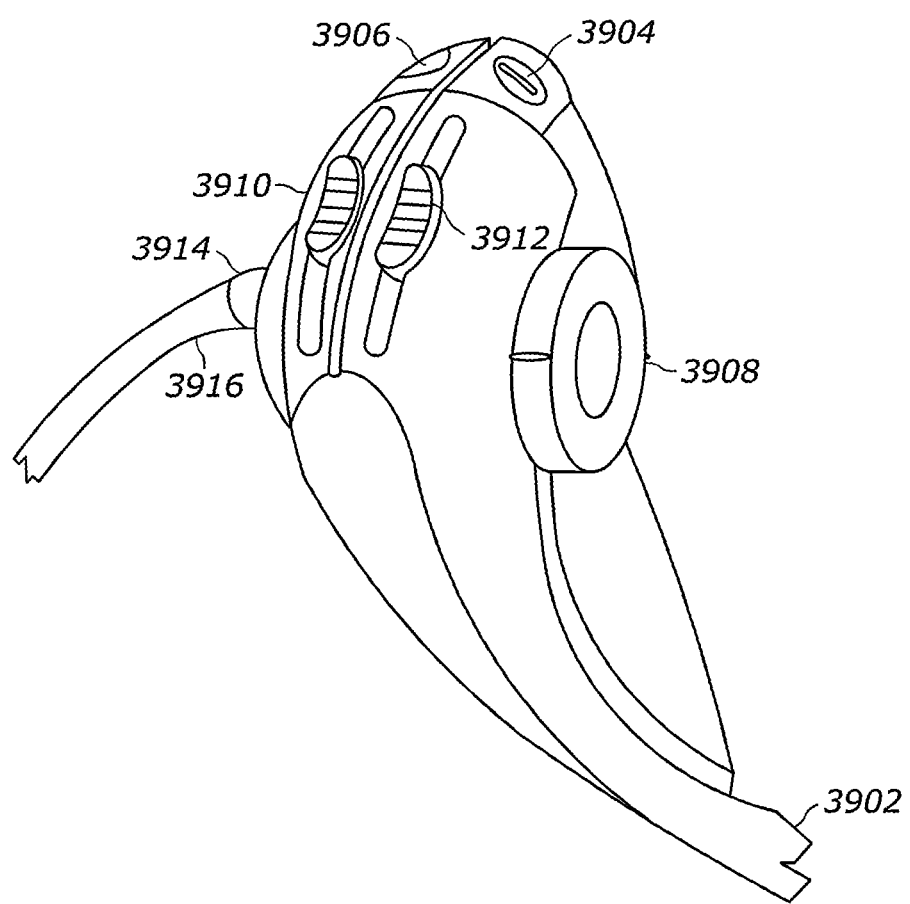
FIG. 36 is a drawing depicting a top perspective view of an illustrative example of a control element for an endoscope.

FIG. 36 depicts a rear perspective view of a further embodiment of a control element. Control element 3902 includes interface elements 3904, 3906, 3908, 3910, 3912. Port 3914 connects to line 3916 which may connect to a computer control element, a display, and/or a computer. In some instances, port 3914 is used to provide suction, air, and/or water, as well as house electronics. Interface element 3906 may be used to actuate photo or video capabilities of the endoscope, while interface 3904 may be used to control audio input. Interface elements 3910, 3912 may be used to control movement of the distal element, for example, via a steering collar (shown in FIGS. 7A-B) in part. Interface element 3908 controls an amount and/or duration of fluid provided to a target area via the endoscope. For example, interface element 3908 may be programmed to deliver predetermined amount of fluid over a predetermined time frame. These settings may be controlled by a user and/or by protocols designed for each use of the endoscope. In particular, a short twist of interface element 3908 may deliver 5 mL bursts of water to the target area.

Figure 37:
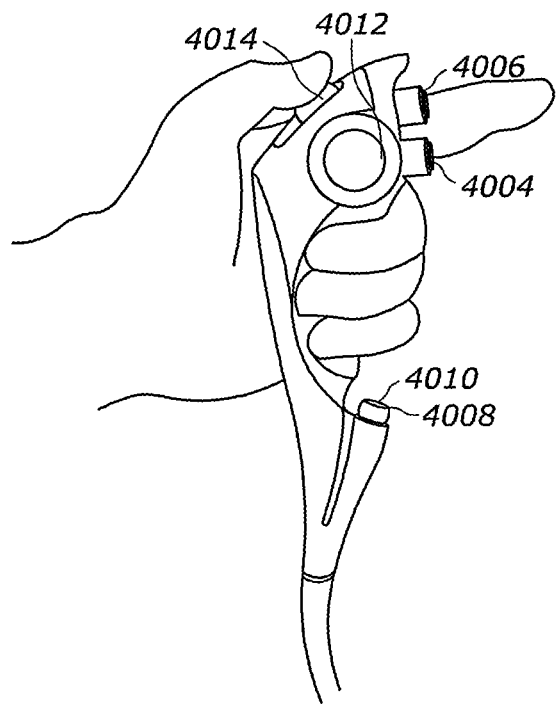
FIG. 37 is a drawing depicting a side perspective view of an illustrative example of a control element for an endoscope.

FIG. 37 depicts a side view of control element and illustrates the ergonomic design of the control element. Port 4006 provides a connector for suction, so that suction can be provided to a target area. Port 4004 provides a connection for fluids which may be delivered to a target area. An amount of fluid and/or type of fluid may be controlled using the interface element 4012. Interface element 4014 controls the positioning of the distal element. Port 4008 provides access to the target area via a conduit running through the elongated element for insertion element 4010.

In some embodiments, there may be a scope stiffening element to allow use of the endoscope in aerodigestive medicine. For example, a wire may be used as a stiffening element in the elongated element.

Additional interface elements may be used to control various aspects of the device. For example, foot pedals may be used to activate and control fluid flows and/or suction, control imaging devices and/or audio devices. Input devices capable of providing information to the various systems may include interface elements, for example, buttons, joysticks, tracker balls, foot pedals, virtual reality devices, goggles, glasses, and the like, sensors, imaging elements, audio elements, and/or any device configured to report a value.

In some embodiments, an interface element may be programmed to interact with a specific a behavior of the operator to achieve a desired outcome. Thus, it may be possible to customize the inputs based on the needs and/or desires of a user and/or a use. For example, some users may prefer a specific configuration of interface elements that combine input from one or both hand and/or one or both feet. Further, some protocols may require specific movements from a user that may make it desirable to alter the inputs so that the user has an increased ability to use their hands for other purposes.

As discussed herein, the elongated element 4107 has a conduit running the length of the endoscope and is adapted to slidingly receive an inserted element, such as biopsy forceps, through port 4106 and into a lumen of the conduit. Control element 4102 also includes port 4110 for connecting to the computer control unit, a computer and/or a display. Ports 4112, 4114 may be configured to deliver fluids and/or such to a target area via the endoscope.

Figure 38:
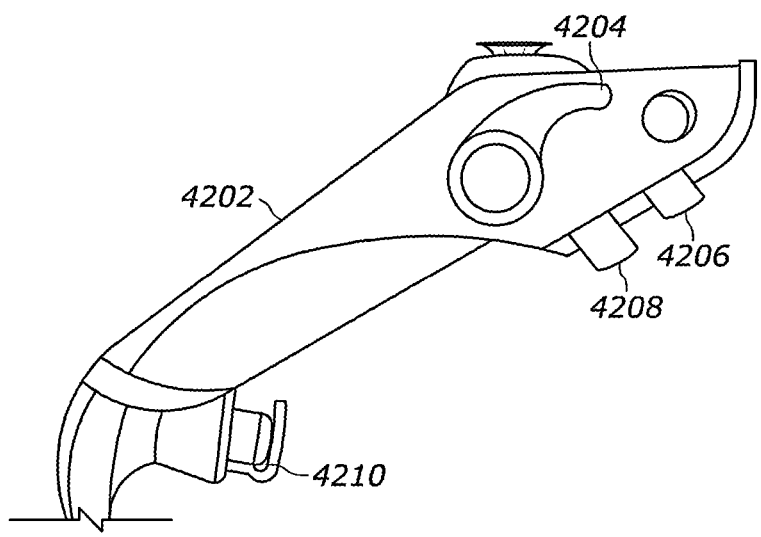
FIG. 38 is a drawing depicting a side perspective view of an illustrative example of a control element for an endoscope.

FIG. 38 depicts a side view of a further embodiment of a control element 4202. Interface elements 4204 may be used to control what is occurring at a target area. Ports 4206, 4208, 4210 may be used to provide inputs and/or remove materials to a target areas.

Figure 39:
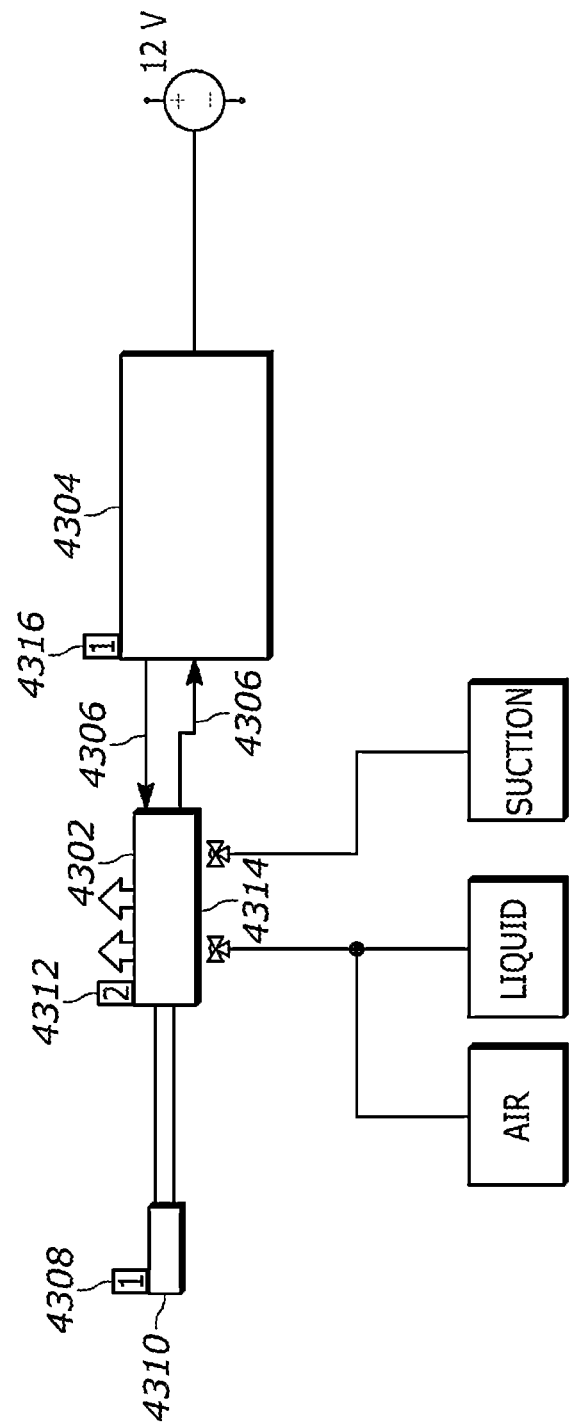
FIG. 39 is a block diagram depicting a system that incorporates an endoscope.

As shown in FIG. 39, control element 4302 may be connected to a computer control element 4304 via cables 4306. Further, the control element may be connected to a computer and/or a display. FIG. 39 depicts positions for a light source for use with the endoscope. In some embodiments, light source 4308 may be positioned proximate and/or in distal element 4310. A light source 4312 may also be positioned in control element 4302. Further, light source 4316 may be positioned on computer control unit 4304. Regardless of the position light may be provided to an illumination element positioned on distal element 4310 using optical fiber.

The computer control element may be designed to sit on a bench. A size of the computer control element may be less than thirty centimeters by 16 centimeters by 10 centimeters. In some cases, the computer control element may be designed to be portable for easy transport.

Figure 40:
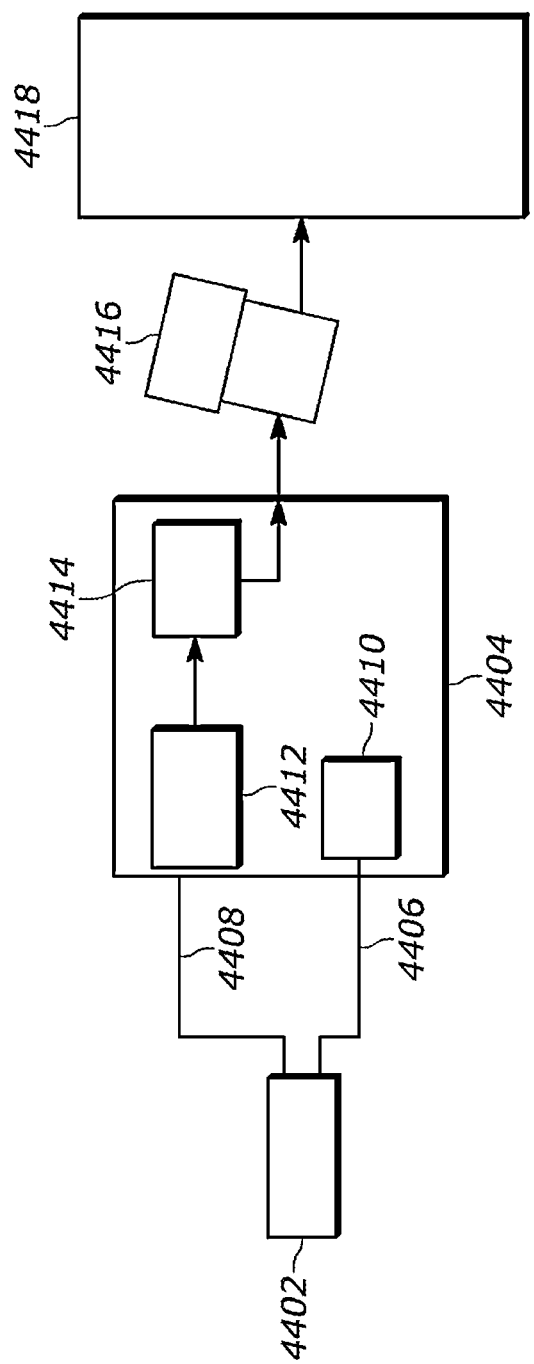
FIG. 40 is a block diagram depicting a system that incorporates an endoscope.

As is shown in FIG. 40, endoscope 4402 may be connected to computer control element 4404 using cables 4408 and optical fiber 4406. In particular, optical fiber 4406 may connect light source 4410 in computer control element 4404 with illumination elements positioned on the scope.

Images captured on the imaging element may be displayed using a computer connected to the computer control element. FIG. 40 depicts an illustrative example of a system including endoscope 4402 coupled to a computer control unit 4404 that includes multiple drivers 4412, 4414 In particular, an optical element controller 4412 is positioned within the computer control element 4404. Data may be transmitted from the optical element controller 4412 to computer 4416 and/or display 4418. In addition, processor 4414 may alter data from the optical element controller prior to providing it to computer 4414.

During a procedure, a screen connected to the computer will be controlled by software such that information and/or images related to a patient and/or procedure are displayed on the screen. As shown in FIG. 41, software may have a setup form 4500 which shows up on a display. Fields on the setup form may vary according to the requirements of the physician, hospital, and/or procedure.

Figure 42:
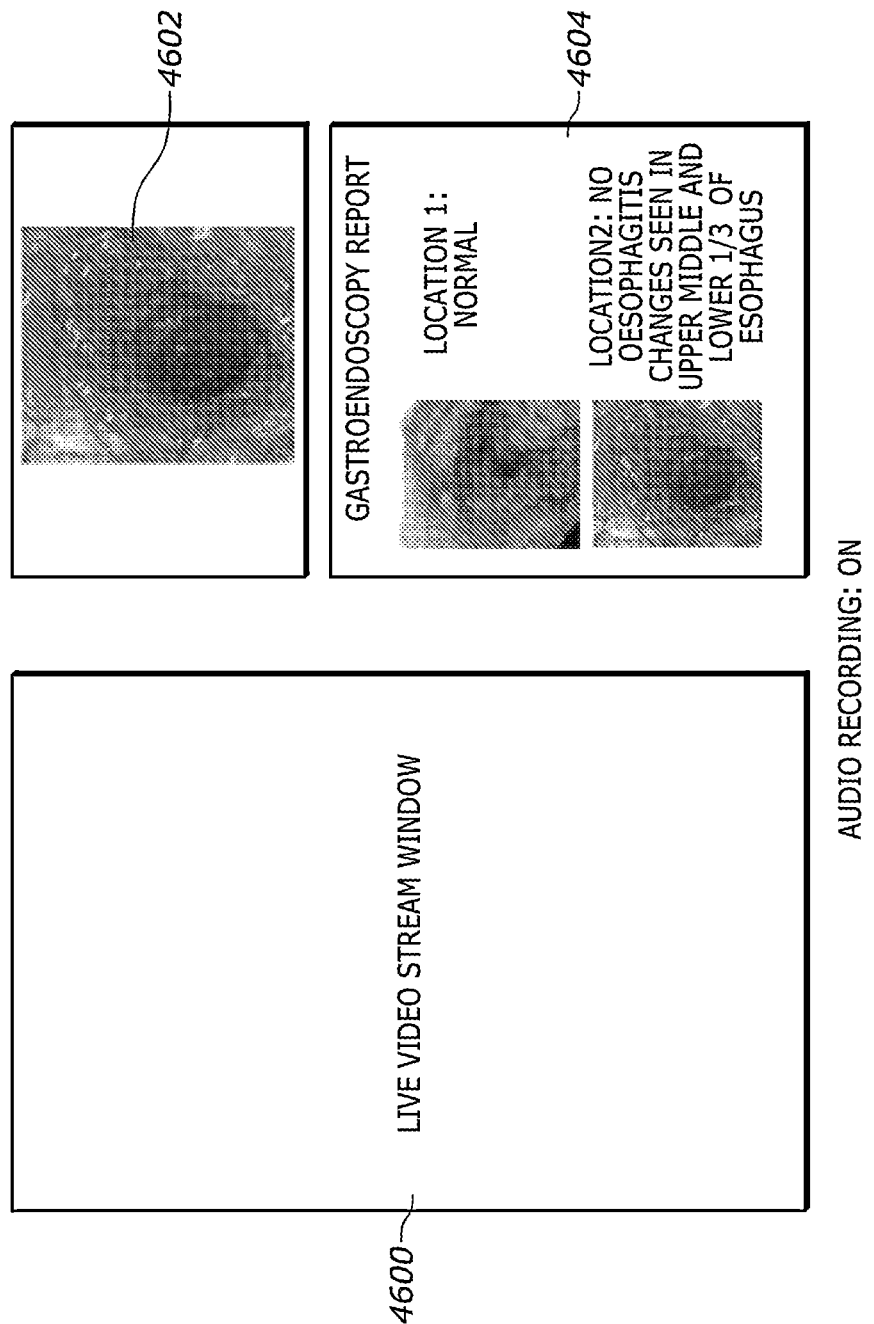
FIG. 42 is a screenshot of a working display for the system.

Images, forms and/or reports may be generated by the computer from one or more inputs from a program, a user, an audio element, an imaging element, and/or sensors. The computer may follow a predetermined algorithm that displays various images depending on the type of procedure performed. For example, FIG. 42 depicts a display for use during a procedure which shows live stream video 4600, a static image 4602 and/or report 4604 These fields may be determined by an end-user, such as a physician, a hospital, or the like. Using the computer, the system may be designed to auto-report. In some instances, this may occur based on a predetermined time interval, movement interval and/or event. Further, auto-reporting may be controlled by an end-user.

Uses for the herein described devices and/or systems may be varied. For example, the devices and/or systems described herein may be used to deliver medications to a target area, remove tissue from a target area, for example to conduct a biopsy, to promote cessation of bleeding/cautery, to remove a foreign body, to collect samples from a target area, in particular bodily fluids, study target areas, in particular the gastrointestinal tract, to evaluate existing and/or potential disease by examining tissues, in particular, pharynx/larynx/esophagus/stomach/small intestine tissues, to diagnose disease or conditions, for example, celiac disease, infection, etc., and/or to manage airways, among others.

The present invention also contemplates the use of the herein disclosed endoscope for measuring an airway, dilation of an airway, gastrointestinal (GI) tract and/or throat as well as placement of enteral feeding tubes and body devices in an airway and GI tract.

The treatment of an airway with the treatment device disclosed in U.S. Pat. No. 9,358,024 involves placing an endoscope. The treatment device is then inserted through or next to the endoscope while visualizing the airways. Alternatively, the visualization system may be built directly into the treatment device using fiber optic imaging and lenses or a CCD and lens arranged at the distal portion of the treatment device. The treatment device may also be positioned using radiographic visualization such as fluoroscopy or other external visualization means. The treatment device which has been positioned with a distal end within an airway to be treated is energized so that energy is applied to the tissue of the airway walls in a desired pattern and intensity. The distal end of the treatment device may be moved through the airway in a uniform painting like motion to expose the entire length of an airway to be treated to the energy. The treatment device may be passed axially along the airway one or more times to achieve adequate treatment. The "painting-like" motion used to exposed the entire length of an airway to the energy may be performed by moving the entire treatment device from the proximal end either manually or by motor. Alternatively, segments, stripes, rings or other treatment patterns may be used.

Sensor elements disposed in the sheath body disclosed in U.S. Pat. No. 8,926,501 may be configured so as to provide sensing contact with a space exterior to the sheath, such as an airway between the sheath and a patient's throat or other body orifice, a blood vessel in a vascular implementations, or other body orifices such as those in the digestive system or excretory system. In some implementations, sensors may be disposed in the body so as to be in contact with a space interior to the sheath, such as a space between the interior surface of the sheath and an inserted endoscope. Sensors may be disposed in the body by attachment to the body on the interior or exterior, such as by use of adhesives or other attachment materials, by molding or forming into the body, or by other attachment or forming methods known or developed in the art.

Physical conditions of interest may include pressure, temperature, flow rate (based on, for example, flow of a gas such as air through an airway or fluid, such as blood, through a flow channel such as an artery or vein), pH, cross-sectional distance measurements (such as measurement of cross-sectional areas of a gas or liquid flow channel, such as the nasal passages or throat), acoustic information (audible sounds or other acoustic information), blood pressure, pulse, and the like.

In an exemplary embodiment, a sensor element comprises a pressure sensor, configured to measure pressure at or near a location being imaged by the endoscope. A pressure sensor may also include one or more additional sensor elements. For example, in one embodiment, a sensor element comprises a pressure sensor and temperature sensor, such as a MEMS based circuit like the SCP1000 device manufactured by VTI Technologies, which is configured to measure both pressure and temperature at or near the location being imaged. Other similar or equivalent devices known or developed in the art may also be used in various implementations.

Research and analysis by the inventors of the technology disclosed herein in the area of airway physiology and airflow characteristics has shown a relationship between pressure values and airflow restrictions in breathing channels, such as through airways like the nose, palate, and rear portion of the mouth and throat. These may be associated with conditions such as airway restriction and sleep apnea, or other breathing issues. While a conventional endoscope may provide some visualization of an airway restriction, additional information of value may be added by acquiring pressure data, acoustic data, body conditions such as blood pressure, pulse, temperature and/or other sensor data simultaneously with visual information such as images or video provided by the endoscope. In particular, it may be advantageous to obtain this additional sensory information and map or fuse it to the associated imaging data obtained by the endoscope camera to provide an image or display of the combined data and image or images in two or three dimensions.

The present invention also encompasses a method for determining properties of a body lumen at different states with an endoscopic instrument as disclosed in U.S. Pat. No. 8,696,547. The method of the '547 patent involves providing a computer having a processor configured to: acquire a first set of 3D image data of a body lumen at a first lumen state; acquire a second set of 3D image data of the body lumen at a second lumen state, the body lumen having a different shape in the second lumen state than in the first lumen state; determine from the first set of previously acquired 3D image data a first property at each location along the body lumen; determine from the second set of previously acquired 3D image data the first property at each location along the body lumen; register the first property at the first lumen state to the first property at the second lumen state at each location along the body lumen, thereby mapping the first property at the first lumen state and the first property at the second lumen state for each location along the body lumen; estimate an endoscopic instrument position of the endoscopic instrument relative to the body lumen when the endoscopic instrument has been advanced into the body lumen; and automatically identify in real time at least one of the following: the first property at the first lumen state based on the endoscopic instrument position and the mapping, and the first property at the second lumen state based on the endoscopic instrument position and the mapping.

The present invention also encompasses a method for continuous guidance of endoscopy during a live procedure as disclosed in U.S. Pat. No. 8,672,836. The method of the '836 patent involves the steps of: a) providing a precomputed data-set based on 3D image data, the data-set including reference information representative of a predefined route through a body organ to a final destination, the reference information including virtual endoscopic (VE) image data representing one or more of the following: 3D organ surfaces, 3D routes through an organ system, and 3D regions of interest (ROIs); b) displaying a plurality of live real endoscopic (RE) images as an operator maneuvers an endoscope within the body organ; c) presenting information, corresponding to an initial reference location along the predefined route, which enables an endoscope operator to move the endoscope toward the reference location; d) invoking a registration/tracking algorithm that registers the VE image data to one or more of the RE images and continuously maintains the registration as the endoscope is locally maneuvered; e) presenting information corresponding to another reference location along the predefined route, which enables the endoscope operator to move the endoscope close to this new reference location; f) repeating steps d)-e) a plurality of times until the endoscope is within the vicinity of the final destination; and g) when the final destination is within the field of view of the endoscope, providing additional information enabling the endoscope operator to decide on a final maneuver for the procedure, the additional information including an icon, other the ROI itself, superimposed on at least one of the VE and RE images to visually indicate a direction from the final destination, including a visual indication of where to penetrate through the wall of the body organ, to the ROI.

The endoscope of the present invention also contemplates a method of collecting and/or sampling body fluids. A body fluid collection device disclosed in U.S. Pat. No. 9,713,461 comprises a longitudinal member having a lumen formed along a longitudinal axis and configured to be inserted through a conduit and/or channel, a flow path in which a suction is acted by the suction section of the endoscope, which is formed to bring the lumen of the longitudinal member in communication with the conduit and/or channel, an accommodating section which is formed in the flow path, and accumulate the body fluid suctioned in the lumen by the suction section of the endoscope, and a sealing member configured to seal a space between the longitudinal member and the channel closer to a distal end of the longitudinal member than the suction port so that a fluid does not flow from the distal end side to a proximal end side of the longitudinal member.

A body fluid collection device configured to be used in combination with an endoscope having a channel and a suction section configured to suction the inside of the channel from a suction port in communication with the conduit and/or channel, the body fluid collection device comprises a longitudinal member having a lumen formed along a longitudinal axis and configured to be inserted through the channel, a flow path in which a suction is acted by the suction section of the endoscope, which is formed to bring the lumen of the longitudinal member in communication with the channel, an accommodating section which is formed in the flow path, and accumulate the body fluid suctioned in the lumen by the suction section of the endoscope, and a sealing member configured to seal a space between the longitudinal member and the channel closer to a distal end of the longitudinal member than the suction port so that a fluid does not flow from the distal end side to a proximal end side of the longitudinal member.

The endoscope of the present invention may be involved in evaluating disease, normal tissues, pharynx/larynx/esophagus/stomach/small intestine as well as disease diagnosis and management of airways (such as but not limited to trachea and bronchi) including endoscopic procedures (such as but not limited to biopsy, balloon dilation and lavage).

A method and system for diagnosing and treating infection or disease, in which an individual takes a photograph of an infected or diseased area of a body using a camera connected to a microprocessor disclosed in U.S. Pat. No. 9,649,013 is contemplated. A photograph may be sent to a diagnosing center having a server with a second microprocessor and a database of photographs correlated with different diseases and infections. The second microprocessor scans the image received from the camera and compares it to the photographs in the database. If a match is found, the second microprocessor then notes the disease or bacteria corresponding to the matching photograph. The second microprocessor then searches an additional database correlated to the match, to further refine the diagnosis. The second microprocessor then searches the second database for a treatment corresponding to the identified disease or bacteria. Once a treatment is identified, information regarding this treatment is automatically sent to the individual's microprocessor.

The endoscope of the present invention may have a shaft connected to a camera, which can record video and still images seen through shaft. The video and still images may be transmitted to a microprocessor via a cable. The video and still images can also be displayed on a display screen. A microprocessor may be connected to a communication device, which can be a modem. The images obtained by a camera may be compared to an initial database stored inside a database connected to microprocessor, and if a match is found, then sent to a second database, accessible over the internet, for a more refined diagnosis. Once the final diagnosis has been made, the diagnosis and possible treatments are sent back to the physician, and can be displayed on a display, or can be communicated in another manner, such as by voice instructions or holographically onto an eyepiece or lenses worn by the physician during the procedure, so that the physician does not have to look away from the procedure to receive the diagnosis. The holographic message could also be projected onto a lens of a microscope, or the endoscope, or even onto a wall or other surface.

The endoscope may have an extension attached to its distal end. In use, an extension can be inserted into the tissue of a patient so that a layer of cells lies on top of the top surface of the extension. This layer can then be illuminated, either from behind, if the extension is translucent, or from the front, by the light source of the endoscope. The layer can be the thickness of a single layer of cells. Thus, the camera takes an image that is essentially a prepared slide for sending to a microprocessor. Thus, the cells of the tissue being examined are more visible and the diagnosis can be made more easily. This procedure also saves the time and expense required in preparation of slides in a laboratory.

A non-invasive and minimally invasive denervation methods and systems for performing the same as disclosed in U.S. Pat. No. 9,649,154 is also contemplated for the present invention. A system and method can be used to denervate at least a portion of a bronchial tree. An energy emitter of an instrument is percutaneously delivered to a treatment site and outputs energy to damage nerve tissue of the bronchial tree. The denervation procedure can be performed without damaging non-targeted tissue. Minimally invasive methods can be used to open airways to improve lung function in subjects with COPD, asthma, or the like. Different sections of the bronchial tree can be denervated while leaving airways intact to reduce recovery times.

A minimally invasive system capable of treating the respiratory system to enhance lung function may be utilized to treat a subject suffering from COPD, asthma, or the like and, thus, the lungs may perform poorly. To decrease air flow resistance to increase gas exchange, the system can be used to perform a denervation procedure.

The instrument can be used to attenuate the transmission of signals traveling along the vagus nerves that cause or mediate muscle contractions, mucus production, inflammation, edema, and the like. Attenuation can include, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs. Decreasing or stopping sensory input from the airways and lungs to local effector cells or to the central nervous system can also decrease reflex bronchoconstriction, reflex mucous production, release of inflammatory mediators, and nervous system input to other cells in the lungs or organs in the body that may cause airway wall edema. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. In some embodiments, the airway inflammation can be decreased a sufficient amount to cause a substantial decrease in airflow resistance and ongoing inflammatory injury to the airway wall. Signal attenuation may allow the smooth muscles to relax, prevent, limit, or substantially eliminate mucus production by mucous producing cells, and decrease inflammation. In this manner, healthy and/or diseased airways can be altered to adjust lung function. After treatment, various types of questionnaires or tests can be used to assess the subject's response to the treatment. If needed or desired, additional procedures can be performed to reduce the frequency of coughing, decrease breathlessness, decrease wheezing, and the like.

Main bronchi (i.e., airway generation) can be treated to affect distal portions of the bronchial tree. In some embodiments, the left and right main bronchi are treated at locations along the left and right lung roots and outside of the left and right lungs. Treatment sites can be distal to where vagus nerve branches connect to the trachea and the main bronchi and proximal to the lungs. A single treatment session involving two therapy applications can be used to treat most of or the entire bronchial tree. Substantially all of the bronchial branches extending into the lungs may be affected to provide a high level of therapeutic effectiveness. Because the bronchial arteries in the main bronchi have relatively large diameters and high heat sinking capacities, the bronchial arteries may be protected from unintended damage due to the treatment.

Nerve tissue distal to the main bronchi can also be treated, such as nerve tissue positioned outside the lung which run along the right or left main bronchi, the lobar bronchii, and bronchus intermedius. The intermediate bronchus is formed by a portion of the right main bronchus and includes origin of the middle and lower lobar bronchii. The distal section can be positioned alongside higher generation airways (e.g., airway generations >2) to affect remote distal portions of the bronchial tree. Different procedures can be performed to denervate a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Each segmental bronchus may be treated by delivering energy to a single treatment site along each segmental bronchus. Nerve tissue of each segmental bronchus of the right lung can be destroyed. In some procedures, one to ten applications of energy can treat most of or substantially all of the right lung. Depending on the anatomical structure of the bronchial tree, segmental bronchi can often be denervated using one or two applications of energy.

Function of other tissue or anatomical features, such as the mucous glands, cilia, smooth muscle, body vessels (e.g., blood vessels), and the like can be maintained when nerve tissue is ablated. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, a portion of an airway of the bronchial tree can be denervated to attenuate one or more nervous system signals transmitted by nerve tissue. Denervating can include damaging all of the nerve tissue of a section of a nerve trunk along an airway to stop substantially all the signals from traveling through the damaged section of the nerve trunk to more distal locations along the bronchial tree or from the bronchial tree more proximally to the central nervous system. Additionally, signals that travel along nerve fibers that go directly from sensory receptors (e.g., cough and irritant receptors) in the airway to nearby effector cells (e.g., postganglionic nerve cells, smooth muscle cells, mucous cells, inflammatory cells, and vascular cells) will also be stopped. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation, mucous cells decrease mucous production, or inflammatory cells stop producing airway wall swelling and edema. These changes reduce airflow resistance so as to increase gas exchange in the lungs, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

Any number of procedures can be performed on one or more of these nerve trunks to affect the portion of the lung associated with those nerve trunks. Because some of the nerve tissue in the network of nerve trunks coalesces into other nerves (e.g., nerves connected to the esophagus, nerves though the chest and into the abdomen, and the like), specific sites can be treated to minimize, limit, or substantially eliminate unwanted damage of other nerves. Some fibers of anterior and posterior pulmonary plexuses coalesce into small nerve trunks which extend along the outer surfaces of the trachea and the branching bronchi and bronchioles as they travel outward into the lungs. Along the branching bronchi, these small nerve trunks continually ramify with each other and send fibers into the walls of the airways.

An activatable element in the form of an energy emitter is configured to damage nerve tissue, such as a vagus nerve branch. Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. There is a constant, baseline tonic activity of the efferent vagus nerve tissues to the airways which causes a baseline level of smooth muscle contraction and mucous secretion.

The energy emitter can ablate the efferent and/or the afferent tissues to control airway smooth muscle (e.g., innervate smooth muscle), mucous secretion, nervous mediated inflammation, and tissue fluid content (e.g., edema). The contraction of airway smooth muscle, excess mucous secretion, inflammation, and wall edema associated with pulmonary diseases often results in relatively high air flow resistance causing reduced gas exchange and decreased lung performance.

The instrument can be delivered through a percutaneous opening in the chest, back, or other suitable location. Potential access locations include between the ribs in the chest, between the ribs in a para-sternal location, between the ribs along the back or side of the subject, from a subxiphoid location in the chest, or through the pre-sternal notch superior to the manubrium. As used herein, the term "percutaneous" and derivations thereof refer generally to medical procedures that involve accessing internal organs via an opening, such as a puncture or small incision in a subject's skin and may involve the use of an access apparatus, such as the access apparatus. The access apparatus can be in the form of a trocar, a cannula, a port, a sleeve, or other less-invasive access device, along with an endoscope. The distal section can be relatively sharp to puncture and pass through tissue. A stylet can be positioned in a lumen in the instrument and can have a relatively sharp tip to directly puncture the skin. After the stylet is inserted into the skin, the instrument can be moved along the stylet through the user's skin into and between internal organs.

The instrument may be visualized using fluoroscopy, computed tomography (CT), thoracoscopy, ultrasound, or other imaging modalities, and may have one or more markers (e.g., radiopaque marks), or dyes (e.g., radiopaque dyes), or other visual features. The visual features can help increase the instrument's visibility, including the instrument's radiopacity or ultrasonic visibility.

An instrument shaft can be made of a generally flexible material to allow delivery along tortuous paths to remote and deep sites. The distal section can be steered or otherwise manipulated using a steering assembly. The distal section can be deflected laterally or shaped into a desired configuration to allow enhanced navigation around thoracic structures. To deliver energy to a treatment site, the distal section can assume a treatment configuration. The treatment configuration can be a serpentine configuration, a helical configuration, a spiral configuration, a straight configuration, or the like. Conventional electrode catheters or ablation catheters can also be used to perform at least some methods disclosed herein.

Figure 3:
FIG. 3 is an image taken from a subject with active furrowing and eosinophilic exudates.

As used herein, the term "energy" is broadly construed to include, without limitation, thermal energy, cryogenic energy (e.g., cooling energy), electrical energy, acoustic energy (e.g., ultrasonic energy), microwave energy, radiofrequency energy, high voltage energy, mechanical energy, ionizing radiation, optical energy (e.g., light energy), and combinations thereof, as well as other types of energy suitable for treating tissue. The energy emitter 209 of FIG. 3 can include one or more electrodes (e.g., needle electrodes, bipolar electrodes, or monopolar electrodes) for outputting energy, such as ultrasound energy, radiofrequency (RF) energy, radiation, or the like. The electrodes can output a sufficient amount of RF energy to form a lesion at the periphery of the airway. To avoid damaging smooth muscle tissue, a lesion can have a depth less than or equal to about 2 mm. In some embodiments, the lesion depth D can be less than about 1 mm to localize tissue damage. Thermal energy emitters can be resistive heaters or thermally conducting elements. To treat tissue with microwave energy, the energy emitter can include one or more microwave antennas. In optical embodiments, the energy emitter includes one or more lenses or reflector(s) capable of outputting light delivered via one or more optical fibers. An external light source (e.g., a lamp, an array of light emitting diodes, or the like) can output light that is delivered through the shaft to the energy emitter. In other embodiments, the energy emitter is a light source, such as a light-emitting diode (LED) or laser diode. Photodynamic agents or light activatable agents can be used to ablate tissue. In yet other embodiments, the energy emitter can include a dispenser (e.g., a nozzle, an orifice, etc.) for delivering a substance (e.g., a chemical agent, a high temperature fluid, a cutting jet, etc.) that kills or damages targeted tissue. Multiple emitters can be used sequentially or simultaneously to treat tissue. For example, an energy emitter in the form of a dispenser can mechanically damage surface tissue while another energy emitter outputs radiofrequency or microwave energy to destroy deep tissue.

For mechanical denervation, the distal section can mechanically damage tissue by cutting, abrading, or tearing nerve tissue. A minimal amount of tissue adjacent to the nerve tissue 45 may also be damaged. The damaged non-targeted tissue can heal without any appreciable decrease in lung function. In embodiments, the distal section comprises a morcellation device.

The distal section can comprise one or more energy absorption devices for absorbing energy from a remote energy source. The remote energy source can be a microwave energy source, a radiofrequency energy source, an ultrasound energy source, or a radiation energy source and can be positioned outside the subject's body or located in another body structure, such as the esophagus, airway (trachea or bronchus), or elsewhere in the subject's body. The distal section can be heated by the remote energy source to a sufficient temperature to damage targeted tissue. Additionally or alternatively, the element can include a reflector to reflect energy from a remote energy source. The reflected energy can create a pattern (e.g., interference pattern) to control the amplitude of energy waves at the target site.

The controller can include one or more processors, microprocessors, digital signal processors (DSPs), field programmable gate arrays (FPGA), and/or application-specific integrated circuits (ASICs), memory devices, buses, power sources, and the like. For example, the controller can include a processor in communication with one or more memory devices. Buses can link an internal or external power supply to the processor. The memories may take a variety of forms, including, for example, one or more buffers, registers, random access memories (RAMs), and/or read only memories (ROMs). The controller may also include a display, such as a screen, and can be a closed loop system, whereby the power to the distal section s controlled based upon feedback signals from one or more sensors configured to transmit (or send) one or more signals indicative of one or more tissue characteristics, energy distribution, tissue temperature, or any other measurable parameters of interest. Based on those readings, the controller can then adjust operation of the distal section. By way of example, the controller can control the amount of energy delivered from the energy source (e.g., one or more batteries or other energy storage devices) to the energy emitter. The sensor can be a temperature sensor. If the temperature of the peripheral tissue of the airway becomes too hot, the distal section can cool the tissue using one or more Peltier devices, cooling balloons, or other types of cooling features. Current sensors or voltage sensors can be used to measure the tissue impedance. Alternatively, the controller can be an open loop system wherein the operation is set by user input. For example, the system may be set to a fixed power mode. It is contemplated that the system can be repeatedly switched between a closed loop mode and an open loop mode to treat different types of sites.

The instrument can also include any number of different types of visualization devices, such as cameras, optical fibers, lenses, or mirrors. Ultrasound or other types of energy-based viewing systems can be used to visualize deep targeted tissues. Surface tissues can be targeted using direct visualization while deeper tissues are subsequently targeted using ultrasound.

As used herein, the term "ablate," including variations thereof, refers, without limitation, to destroying or permanently damaging, injuring, or traumatizing tissue. For example, ablation may include localized tissue destruction, cell lysis, cell size reduction, necrosis, or combinations thereof. In the context of pulmonary ablation applications, the term "ablation" includes sufficiently altering nerve tissue properties to substantially block transmission of electrical signals through the ablated nerve tissue. Ablating all of the nerve trunks along the airway prevents nerve signals from traveling distally along the airway and causes the smooth muscle to relax to open the airway.

In RF ablation, RF energy causes heating of the nerve tissue and, ultimately, the formation of the lesion. The nerve tissue is destroyed without removing a significant amount of airway tissue, if any, to preserve the integrity of the airway. The lesion can be left in the body to avoid potential complications from removing airway tissue. The healthy airway wall prevents gas escape across the airway wall. The smooth muscle and interior lining of the airway can remain substantially undamaged to allow mucociliary transport and other bodily functions that are important to overall health. This reduces the recovery time and avoids or mitigates problems associated with surgical techniques of removing or cutting through the airway wall. In contrast to lung resection procedures in which entire airways are severed and removed, an intact denervated airway can also ensure that distal regions of the lung continue to function.

Large lesions can extend through the airway wall and can be formed to destroy unwanted tissue (e.g., cancerous tissues) positioned along the inner surface. Differential cooling can be used to form lesions buried deep within the sidewall, spaced apart from the interior and exterior surfaces of the airway, or any other suitable location. The instrument can cool tissues to keep the nontargeted tissue below a temperature at which cell death occurs. In some embodiments, the distal section has a cooling member (e.g., a cooling balloon) that absorbs thermal energy to keep nontargeted regions of the airway wall at or below a desired temperature. The shape and size of lesions can also be adjusted as desired.

Natural body functions can help prevent, reduce, or limit tissue damage. If the bronchial artery branch is heated, blood within the blood vessels can absorb the thermal energy and can then carry the thermal energy away from the heated section of the branches. The lesion can surround a region of the blood vessel 130 without destroying the vessel. After the treatment is performed, the bronchial artery branches can continue to maintain the health of lung tissue.

The lesion depth can be kept at or below a desired depth by controlling the amount of delivered energy. To avoid reaching smooth muscle, the depth can be equal to or less than about 3 mm, 2 mm, or 1 mm. For thick airway walls, the lesion depth can be equal to or less than about 3 mm. For medium size airway walls, the lesion depth can be equal to or less than about 2 mm. In young children with thin airway walls, the lesion depth can be equal to or less than about 1 mm. The lateral dimensions (e.g., width, length, etc.) of the lesion can be adjusted to ensure that targeted tissue is ablated.

The instrument can be delivered along the trachea, esophagus, pharynx, or other body structure in the vicinity of the treatment site. For example, the instrument can extend through one or more organs to position an energy emitter 314 proximate to the targeted tissue. The instrument can cool interior regions of the airway wall to cause the formation of the lesion at the outer periphery of the airway wall. For radiofrequency ablation, the RF energy can travel between bipolar electrodes. Tissue impedance causes heating that can reach sufficiently high temperatures to cause cell death. To protect non-targeted tissues (e.g., interior tissue), the instrument can cool the airway to keep the nontargeted tissue below a temperature at which cell death occurs.

Thermal energy can be absorbed by the instrument to keep the exterior regions of the airway wall at or below a desired temperature. Both instruments can provide cooling to form lesions generally midway through the airway wall. The amount of energy delivered and cooling capacity provided by the instruments can be adjusted to shape and form lesions at different locations.

At least one of the instruments can be adapted to tunnel through tissue or between adjacent structures to allow it to reach the desired location, for example, along the bronchi. Additionally or alternatively, the instruments may be adapted to adhere to or slide smoothly along tissue or to be urged against a structure (e.g., trachea, esophagus, and/or bronchi) as the instrument is advanced.

A wide range of different types of guides can partially or completely surround a structure, such as the esophagus, trachea, or bronchus. Guides may include, without limitation, a plurality of arms (e.g., a pair of arms, a set of curved or straight arms, or the like), a ring (e.g., a split ring or a continuous ring), or the like.

Cartilage rings or cartilage layers typically have a significantly larger electrical resistance than airway soft tissue (e.g., smooth muscle or connective tissue). Airway cartilage can impede the energy flow (e.g., electrical radiofrequency current flow) and makes the formation of therapeutic lesions to affect airway trunks challenging when the electrode is next to cartilage. The electrodes can be positioned to avoid energy flow through cartilage. For example, the electrode can be positioned between cartilage rings. Most or substantially all of the outputted energy can be delivered between the rings in some procedures. Tissue impedance can be measured to determine whether a particular electrode is positioned next to a cartilage ring, in an intercartilaginous space, or at another location.

The instrument may have a lumen to receive a stylet to straighten and stiffen the preshaped distal section during introduction. After insertion, the stylet can be withdrawn to allow the preshaped distal section to assume a treatment configuration (e.g., a spiral configuration, a helical configuration, or the like). Alternatively, the distal section may be relatively flexible and straight during introduction. A stylet having a shape corresponding to a desired shape may be inserted into the instrument to impart the desired shape to the distal section. In a further embodiment, the instrument may be shapeable or steerable using an actuator at its proximal end to allow it to be steered so as to surround the target tubular structure. Various steering mechanisms can be used, including, for example, one or more pull wires anchored to a distal tip at a point offset from the center line. The wire(s) can extend slidably through one or more lumens in the instrument to the proximal end where they may be tensioned by an actuator so as to deflect the distal section.

A system for non-invasively denervating a bronchial tree may include an external energy source connected to an energy delivery system. The external energy source can emit a beam of radiation to targeted tissue, such as nerve tissue. The beam of radiation can destroy the targeted tissue. The system can include, or be in the form of, a CyberKnife® Robotic Radiosurgery System from Accuray®, a Tomo-Therapy® radiation therapy system, or similar type of systems capable of targeting moving tissue, thereby mitigating or limiting damage to non-targeted tissue.

Beam radiation may be delivered from different remote locations to damage deep nerve tissue without damaging intervening tissues. The source of beam radiation may be a beam emitter of an external beam radiotherapy system or a stereotactic radiation system. Because the lungs and bronchi move as the subject breathes, the system can be adapted to target moving tissues. By positioning the radiation beam emitter at various locations relative to the patient's body, such systems may be used to deliver a radiation beam from various angles to the targeted nerve tissue. The dose of radiation given to intervening tissues may be insufficient to cause injury, but the total dose given to the target nerve tissue is high enough to damage (e.g., ablate) the targeted tissue.

Ultrasound can be used to damage targeted tissue. High intensity focused ultrasound may be used to target and damage the nerve tissue. The external energy source can be a HIFU emission device. Alternatively, a catheter, an intra-luminal instrument, or other type of instrument for insertion into the body can include a HIFU emission device. Such embodiments are well suited for delivery through another body structure, such as the esophagus or airway, to treat a target tissue of an airway. The HIFU instrument may include ultrasound imaging capability to locate the targeted tissues. The HIFU instrument can emit a plurality of ultrasound "beams" from different angles toward the target tissues. The intensity of any one of the beams can be insufficient to damage intervening tissues. The beams can interfere at the target site and together have sufficient magnitude to damage the target nerve tissue.

The HIFU-based systems can be adapted to target moving tissues. For example, such systems may have a computer-controlled positioning system which receives input from an ultrasound or other imaging system and commands a positioning system in real time to maintain the HIFU device in a fixed position relative to the target structure.

Instruments disclosed herein may be entirely or partially controlled robotically or by a computer. Instruments may be attachable to a computer-controlled robotic manipulator which moves and steers the instruments. Robotic systems, such as the da Vinci® Surgical System from Intuitive Surgical or the Sensei Robotic Catheter system from Hansen Medical, Inc., or similar types of robotic systems, can be used. The instruments can have a proximal connector (e.g., an adaptor mechanism) that connects with a complementary fitting on the robotic system and links movable mechanisms of the instrument with control mechanisms in the robotic system. The instrument connector can also provide electrical couplings for wires leading to energy emitters, electrodes, microwave antennae, or other electrically powered devices. The instrument may further include sensor devices (e.g., temperature sensors, tissue impedance sensors, etc.) which are also coupled via the connector of the robotic system. The robotic system can include a control module that allows the physician to move and activate the denervation instrument while visualizing the location of the instrument within the chest, for example, using thoracoscopy, fluoroscopy, ultrasound, or other suitable visualization technology. The instrument may also be computer controlled, with or without robotic manipulation. A computer may receive feedback (e.g., sensory data) from sensors carried by the instrument or elsewhere to control positioning, power delivery, or other parameters of interest. For example, in energy-based denervation embodiments, a computer may be used to receive temperature data from temperature sensors of the instrument and to control power delivery to avoid overheating of tissue.

The instruments can access sites through blood vessels, as well as external to the organs. Robot surgery (including robotic catheter systems), natural orifice access methods, and minimally invasive access methods such as using trocar access methods and thoracoscopy have provided clinicians with access procedure locations within the human body and also minimized patient morbidity and complications due to surgery.

The assemblies, methods, and systems described herein can be used to affect tissue which is located on the outside of hollow organs, such as the lung, esophagus, nasal cavity, sinus, colon, vascular vessels and the like or other solid organs. Various types of activatable elements (e.g., energy emitters) can be utilized to output the energy. The activatable elements can be sufficiently small to facilitate percutaneous delivery to minimize or limit trauma to the patient.

The embodiments disclosed herein can treat the digestive system, nervous system, vascular system, or other systems. The treatment systems and its components disclosed herein can be used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue, the bronchial tree, or the like. Access techniques and procedures used to provide access to a target region can be performed by a surgeon and/or a robotic system. Those skilled in the art recognize that there are many different ways that a target region can be accessed.

The present invention also contemplates accessory devices which may be involved, for example but not limited to, cessation of bleeding/cautery or removal of a foreign body. An accessory device is disclosed in U.S. Pat. No. 8,007,432 and can include an insertion member and a control wire. The insertion member can have a lumen for receiving a tool therethrough, such as an endoscope. The control wire can be coupled to the insertion member and have a distal portion extending distally from the insertion member and be adapted to receive and to manipulate a tool extending through the insertion member. The control wire can have a wide variety of configurations, and in certain exemplary embodiments the control wire can be slidably received in one or more control wire lumens formed through the insertion member. In use, the control wire can be manipulated, for example by axially sliding the control wire in one or more control wire lumens to control a tool.

The accessory device can have a variety of configurations, but in the illustrated embodiment the accessory device includes an insertion member in the form of an elongate sheath and an accessory channel. As shown, the elongate sheath can have a distal end with a control wire coupled thereto and a proximal end with a handle and a control mechanism coupled thereto. The elongate sheath can have an endoscope disposed therethrough. The distal face of the endoscope can have a viewing instrument, for example a lens, one or more lighting elements, for example lights or fiber optics, and a lumen formed therein for receiving one or more tools, such as viewing instruments, graspers, cutting devices, irrigation devices, and so on. The elongate sheath can also have a mating element such as a track for mating with a complementary mating element formed on the accessory channel, such as a rail. In addition, the elongate sheath can have one or more control wire lumens formed therein and extending between the proximal and distal ends thereof. The control wire can be slidably disposed in the control wire lumens. The control mechanism can be coupled to the control wire and can be adapted to move the control wire, for example, by manipulation of a knob. Movement of the control wire can include, for example, axially sliding the control wire within one or both of the control wire lumens or axially rotating the control wire. In use, movement of the control wire can be effective to manipulate a tool. The tool, for example, can extend distally from the lumen in the endoscope, or from the accessory channel, or the tool can be separate from or spaced apart from the elongate sheath. The manipulation can take many forms, but as one example, a portion of the tool can be pulled into a viewing window of the endoscope.

As one skilled in the art will understand, the accessory device need not include an accessory channel. For example, the insertion member can be in the form of an elongate sheath with a control wire coupled thereto. In such a case, the elongate sheath need not include a mating element such as a track adapted for mating to the accessory channel. In use, movement of the control wire can be effective to manipulate a tool extending distally from a lumen formed in an endoscope, such as the lumen in the endoscope. Further, one skilled in the art will also understand that it is not necessary to include an elongate sheath or an accessory channel. For example, an alternate embodiment of an accessory device can have an insertion member in the form of an endoscope. As shown, a lumen is formed in the endoscope for receiving a tool therethrough and the distal end of the endoscope has a viewing element and a first and second lighting elements. The endoscope may have a first and second control wire lumens formed therein. In use, the control wire can be moved to manipulate a tool extending distally from the lumen and/or a tool adjacent to the accessory device, such as another tool disposed at the surgical site.

The accessory device, as well as any other exemplary accessory devices previously described, can have a variety of other configurations, as one skilled in the art will understand. For example, the accessory device can have multiple accessory channels, lumens for receiving tools, and/or elongate sheaths. On the other hand, the accessory device need not receive a tool, and instead the control wire can be adapted to manipulate a tool inserted separately to the surgical site within the body. Any of the previously described lumens, such as an accessory channel lumen and/or endoscope lumen, can receive surgical materials, irrigating fluids, antiseptic agents, or organic substances, etc., therethrough in addition to or instead of tools. The accessory device can have multiple control wires which can be movable within control wire lumens and/or fixedly attached to the accessory device. The control wires can be arranged to provide multiple loops or arcs at the distal end of the accessory device, and/or can be arranged in a fashion similar to that of a single control wire. In some embodiments, control wire lumens can be associated with the accessory channel instead of or in additional to elongate sheath. A wide array of further variations will be apparent to those skilled in the art.

The present invention also provides methods for manipulating a tool. In one exemplary method, an accessory device such as the accessory device can be positioned at a surgical site. The accessory device can be positioned in the body by inserting the distal end of the accessory device into a natural orifice such as the mouth, or through an incision made in the body. The accessory device can be advanced distally through a body lumen to a desired position. The insertion may be associated with or preceded by any number of procedures to lubricate, flex, shape, measure, steer, turn, rotate, and/or guide the accessory device into the body. The insertion may also be assisted by or performed with a viewing instrument such as an endoscope for showing the path of the accessory device within the body.

In other embodiments, inserting the accessory device can include inserting an endoscope through an elongate sheath, and mating an accessory channel to an elongate sheath. For example, the rail of the accessory channel can be slidably mated to the track of the elongate sheath, and the accessory channel can be advanced to a desired position along the elongate sheath. Such mating can be performed at any time, including before and after part of the accessory device is inserted in the body. After it is mated, the accessory channel can be unmated, e.g., by sliding the accessory channel proximally along the elongate shaft, and re-mated any number of times to re-introduce the accessory channel or to introduce other accessory channels.

Surgical tools as well as materials can be inserted through one or more lumens in the accessory device. For example, a tool can be inserted through the elongate sheath, through a lumen formed in an endoscope disposed in the elongate sheath, and/or through the accessory channel. Multiple tools can be inserted through a single lumen or through separate lumens. Moreover, as will be apparent to those skilled in the art, a tool can also be inserted into the body separately from the accessory device, for example, not through any lumen formed therein. A tool can be advanced beyond the distal end of the elongate sheath and can be positioned, articulated, and maneuvered at the surgical site, as may be called for by a surgical procedure.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized.

This can be done by any number of ways known to those skilled in the art including beta or gamma radiation, ethylene oxide, or steam.

The invention also contemplates the use of the herein disclosed endoscope to study the gastrointestinal (GI) tract, in particular visualization of the GI tract contents and abnormalities as well as measurement of the GI tract. A medical system disclosed in U.S. Pat. No. 9,675,526 for facilitating installation of a PEG device in a patient's body by utilizing an endoscope is contemplated. Such a system comprises a needle configured to be disposed within an endoscope lumen of the endoscope and moveable along a longitudinal axis relative to the endoscope, wherein the needle includes a needle lumen extending therethrough; a safety cap for being placed on the outside of the patient's body, the safety cap having a cap lumen extending longitudinally therethrough, the cap lumen sized and configured to receive and secure the needle such that the needle lumen and cap lumen are in fluid communication, the cap lumen sized and structured to frictionally engage the needle to secure the needle to the safety cap; and a wire sized and configured to extend completely through the cap lumen and through at least a portion of the needle lumen.

The endoscope is generally flexible while retaining sufficient rigidity to allow it to be pushed through a patient's body toward the target site. The type of endoscope may be configured to extend through a patient's mouth, the upper GI tract, and out through a hole in the patient's abdomen. The length of the endoscope may be approximately 160 cm; however, other lengths could also be used that are long enough to extend out of the mouth, through the upper GI tract, and through the patient's abdomen. Thus, it will appreciated that various lengths could apply to patient's having various body sizes. Known percutaneous endoscopic gastrostomy devices capable of being pulled through the GI tract by a wire having a looped end can also be used. Additionally, other tube-like devices for extending through tissue can also be used, including PEG devices and other devices that can be pushed through the upper GI tract over a guidewire.

The present invention also contemplates injection of medication via the endoscope of the present invention, preferably with a medical fluid device. Typical of medical fluid devices is a vascular access device that allows for the introduction of medication, antibiotics, chemotherapeutic agents, or a myriad of other fluids, to a previously established IV fluid flow system. Alternatively, the access device may be used for withdrawing fluid from the subject for testing or other purposes. The presence of one or more access devices in the IV tubing sets eliminates the need for phlebotomizing the subject repeatedly and allows for immediate administration of medication or other fluids directly into the subject.

Several different types of access devices are well known in the medical field. Although varying in the details of their construction, these devices usually include an access site for introduction or withdrawal of medical fluids through the access device. For instance, such devices can include a housing that defines an access opening for the introduction or withdrawal of medical fluids through the housing, and a resilient valve member or gland that normally closes the access site. Beyond those common features, the design of access sites varies considerably. For example, the valve member may be a solid rubber or latex septum or be made of other elastomeric material that is pierceable by a needle, so that fluid can be injected into or withdrawn from the access device. Alternatively, the valve member may comprise a septum or the like with a preformed but normally closed aperture or slit that is adapted to receive a specially designed blunt cannula therethrough. Other types of access devices are designed for use with connecting apparatus employing standard male luers. Such an access device is commonly referred to as a "luer access device" or "luer-activated device," or "LAD." LADS of various forms or designs are illustrated in U.S. Pat. Nos. 6,682,509, 6,669,681, 6,039,302, 5,782,816, 5,730,418, 5,360,413, and 5,242,432.

The present invention also contemplates use of the endoscope for a biopsy. In particular, an additional biopsy needle attached to the endoscope of the present invention is contemplated. A biopsy needle having a longitudinal channel formed within an inner conductor of a coaxial antenna is disclosed in U.S. Pat. No. 9,351,713. The coaxial antenna terminates in a rigid insertion tip e.g. a ceramic cone that is insertable into biological tissue. Microwave energy (e.g. having a frequency of 1 to 100 GHz) delivered to the coaxial antenna is emitted at the insertion tip. The insertion tip may be arranged to match the impedance of the coaxial antenna to a predetermined tissue impedance. The emitted radiation can be used to measure properties of or treat (e.g., ablate) tissue at the insertion tip. Needle biopsy apparatus is also disclosed, in which a microwave energy is controllably delivered to a needle from a microwave generator. The apparatus may include an impedance tuner to dynamically match the impedance of the needle with tissue at the insertion tip.

According to one aspect of the invention, there may be provided a biopsy needle insertable into tissue for introducing or extracting a sample therefrom, the needle having an elongate body terminating with an insertion tip, a longitudinal channel formed within the body for transporting the sample, and a coaxial antenna comprising an inner conductor and an outer conductor coaxial with the inner conductor and separated from it by a dielectric material, wherein the coaxial antenna is arranged to couple microwave energy to/from tissue at the insertion tip, and the channel is formed within the inner conductor or in an outer portion of the outer conductor. The inner conductor may be a conductive layer along an inside wall of the channel. Preferably, the inner conductor is a conductive layer (tube) that defines the channel. Preferably, the outer conductor comprises a conductive layer formed on the outer surface of the elongate body. The outer conductor may comprise a conductive layer formed on the dielectric material and an annular or part annular channel formed on that conductive layer. The coupled microwave energy may be selectable either to measure properties of tissue at the insertion tip or to ablate tissue at the tip.

In another aspect of the invention, there may be provided needle biopsy apparatus comprising a biopsy needle as described above and a microwave power source arranged to deliver microwave frequency energy to the coaxial antenna in the needle in order to measure and/or ablate tissue at the insertion tip of the needle. The apparatus may include a dynamic impedance tuner arranged to adjust the impedance of the needle e.g. to match the impedance of the tissue at the insertion tip in order to ensure even (uniform) energy delivery into the tissue. This aspect of the invention offers an advantage in that it enables uniform ablation of the channel through which the antenna is inserted to prevent the occurrence of seeding. The ability to dynamically match into various tissue structures prevents uneven ablation due to variations in matching to various tissue types as the tip of the antenna moves through the various structures.

In other words, the needle antenna described in this specification can couple microwave frequency energy into a co-axial structure for the purpose of making tissue type/state measurements, and/or for performing controlled tissue ablation, and has a hollow tube center conductor to enable tissue biopsies to be performed before, after, or during the tissue ablation process. The structure disclosed in the current invention may, therefore, be considered as a tri-functional needle antenna. The frequency of choice used in the current invention, and the microwave aspects of the design of the tri-functional antenna structure makes it possible to measure information regarding the state of the biological tissue at the same location (position) as where the tissue biopsy is to be physically taken, i.e. at the distal tip.

In this specification, microwave frequency means a frequency range of between 1 GHz to 100 GHz, preferably 5 GHz to 60 GHz. Higher frequencies, e.g. up to 200 GHz may also be used. More preferably, the frequency source used operates at a frequency of between 14 GHz and 15 GHz, and, even more preferably, operates at a spot frequency of 14.5 GHz.

It may also be desirable to use a dynamically adjustable tuning filter, for example, a waveguide cavity containing three tuning stubs with a spacing of a quarter of the guide wavelength at the frequency of interest, to create a conjugate match between the distal tip of the needle antenna and the load presented by the biological tissue structure. It should be understood that the tuning filter is positioned between the output from the power amplifier and the distal tip of the needle antenna to enable the output impedance of the amplifier to be matched to the input impedance of the tuning filter, and the output impedance of the tuning filter to be matched to the impedance of the biological tissue. This feature enables the needle antenna to be used to perform controlled ablation of a volume of cancerous tissue or to perform controlled ablation (or sealing) of the needle track (or channel).

The ability of the needle antenna to convey information back to the measurement system to allow dynamic impedance matching to be performed between the changing tissue impedance and the generator enables the energy delivered into the various tissue structures that exist along the track between the site where the tissue biopsy (or the tumor ablation) takes place and the outside world to be automatically regulated to provide uniform tissue ablation of healthy tissue structures en route, i.e. it may be desirable to ablate a channel of 4 mm diameter of healthy tissue along the track (or channel) to prevent the seeding of cancerous cells. The ability of the needle antenna structure to allow for the mode of operation described above to be performed may be an additional feature of the current invention.

The invention may not be limited to using a single frequency source for performing controlled ablation and making dielectric measurement. A plurality of frequency sources may be used. For example, it may be advantageous to use a lower microwave frequency, for example 1 GHz to 10 GHz, for performing controlled ablation, and a higher microwave frequency, for example, 20 GHz to 100 GHz, for performing dielectric measurements. The embodiments of the invention described below use a single frequency source operating at 14.5 GHz, which has the advantage of producing a high energy density for controlled ablation of small tumors and effective track (or channel) sealing, and a small enough radiation distance to allow for dielectric measurements that are localized to the end of the distal tip to be performed. The advantage of using lower microwave frequencies for tumor ablation is that the larger penetration depths associated with low frequency microwave energy may be beneficial in terms of producing effective ablation of large tumors, and the advantage of using higher microwave frequencies for dielectric measurement is that the small radiation distances associated with high frequency microwave energy may be beneficial in terms of effectively performing local tissue measurements that are unaffected by surrounding tissue structures.

A surgical location monitoring system and method disclosed in U.S. Pat. No. 9,566,123 may be adapted for the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipment through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience, therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data ("CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "scan," "fiducial reference", "fiducial location", "marker," "tracker" and "image information" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system that produces a quantitative spatial representation of a patient. The term "fiducial reference" or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site. The term "marker" or "tracking marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. The tracker may include a non-stereo optical camera or a stereo camera pair, which may operate in the visible or infrared region of the spectrum. The term "image information" is used in the present specification to describe information obtained by the tracker, whether optical or otherwise, about one or more tracking markers and usable for determining the location of the markers and their orientation and movement continually in 'real time' during a procedure.

Data communication between a central processor and system memory, which may include read-only memory (ROM) or flash memory, and random access memory (RAM). RAM is generally the main memory into which operating system and application programs are loaded. ROM or flash memory may contain, among other software code, Basic Input-Output system (BIOS), which controls basic hardware operation such as interaction with peripheral components. Applications resident with computer system are generally stored on and accessed via computer readable media, such as hard disk drives, optical drives, a floppy disk unit, or other storage medium. Additionally, applications may be in the form of electronic signals modulated in accordance with the application and data communication technology when accessed via a network modem or interface or other telecommunications equipment (not shown).

A storage interface, as with other storage interfaces of computer system, may connect to standard computer readable media for storage and/or retrieval of information, such as a fixed disk drive. The fixed disk drive may be part of a computer system or may be separate and accessed through other interface systems. A modem may provide direct connection to remote servers via telephone link or the Internet via an Internet service provider (ISP). A network interface may provide direct connection to remote servers via direct network link to the Internet via a POP (point of presence). A network interface may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on), including hardware components, which alternatively may be in communication with associated computational resources through local, wide-area, or wireless networks or communications systems. The hardware components may be directly connected or remotely connected with computing resources. Software source and/or object codes to implement the present disclosure may be stored in computer-readable storage media such as one or more of a system memory, fixed disk, optical disk, or floppy disk. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The present invention also contemplates microdot projector mapping of lumen based organs via the endoscope of the present invention. For example, a probe that had a microdot projector may fit through a channel or attached the tip of a camera.

US Patent Publication 20160296692 discloses a system for injecting fluid to a patient. The system provides manual or automatic verification and identification of the fluid to be injected, prior to, during or after injection. The system includes: a fluid having at least one active compound and at least one tracer compound; an injector configured to deliver the fluid to the patient through a fluid path set; at least one sensor coupled to at least one of the syringe, the injector, or the patient, configured to measure at least one property of the tracer in the fluid, and a feedback path to adjust at least one injection parameter of the injector based on at least one measurement from the at least one sensor.

In certain embodiments, the at least one sensor may be coupled to a tissue section of a patient, such as, for example a dermal tissue section of a patient. In other embodiments, the at least one sensor may be associated with an internal tissue section of the patient, such as where the at least one sensor is on an endoscope, catheter or other medical device inserted within the patient. According to various embodiments, the at least one sensor may be configured to measure in vivo at least one property of the injection fluid such as, for example a concentration of the tracer compound at a site within the patient near the tissue section, a location of the tracer compound within a vascular system of the patient near the tissue section, an extravasation of the tracer compound outside of the vascular system of the patient near the tissue section, or combinations of any thereof.

Microdots and micro-labels may be printed or laser-etched to the surface of the syringe barrel for proper identification. Microdots are microscopic particles, which are typically about one thousand microns in size and include alpha-numeric sequences. The microdots may be printed or laser-etched to a surface to form a barcode-like structure. Various sensors may be used to extract data about the barcode-like structure. Additionally, microdots can include voids within molded dots that reflect various wavelengths of light in readily identifiable patterns. The injector may include a light source at a specific wavelength and sensors configured to measure the predefined reflection. The type of reflection could be used to provide additional information about the syringe or fluid solution. The information may be used for identification and authentication purposes.

US Patent Publication 20050221279 discloses a method for creating chemical sensors using contact-based microdispensing technology. Contact based rigid pin tool technology is utilized to print one or more indicator chemistries on an optical array or a disposable sheath configured on such arrays. Each indicator chemistry contains predetermined material, such as, light energy absorbing dye(s), optically responsive particles, etc., whose optical characteristics change in response to the target ligand or analyte. By spectrally monitoring such changes using fluorescence and/or absorption spectroscopy, detection and/or quantitation of the target ligand or analyte can be obtained.

For in vivo applications it is desirable to have the sensor portion contained in a probe capable of accessing the desired sample. The sensor, for example, can be incorporated in a mechanical periodontal probe for sampling the gingival crevicular fluid and saliva; a needle for accessing tissue; a catheter, endoscope, or guidewire for monitoring blood constituents; a cone penetrometer for making soil gas measurements; or a down well sampler for groundwater monitoring, among others. A fiber optic bundle is a natural choice for these applications, since fibers can guide light long distances with minimal loss of intensity and are very compact. An optical array, such as a standard fiber imaging bundle, may contain 1000's of individually clad optical fibers in a small diameter bundle (<500 .mu.m). Since each microdot overlays at least one imaging fiber the orientation (i.e. rotation) of the bundle tip relative to the rigid tool printing element becomes less important, making sensor manufacture much easier and allowing many more indicator microdots to be placed in a given area. The microdots can either be printed directly on the distal end of the fiber bundle or printed on the tip of a disposable sleeve (e.g. plastic) that can be slipped over the end of the imaging fiber bundle.

A user can create and visualize a customized pattern of microdots simply by using a drag-and-drop tool from a palette of up to conceivably 1596 color-coded chemistries. Each chemistry is color-coded, as specified by the user, within the software and mapped to one well in a standard well plate. The user can save this pattern to a file, or load a previously saved pattern to the pattern editor. After placing dots on a pattern editor template, individual dots can be selected and the position finely tuned by adjusting coordinates. The order in which microdots are printed is determined by the placement order in the pattern editor. In multi-chemistry printing, all microdots of like chemistries are printed in sequence.

An automated routine executes a single printing cycle for each indicator chemistry specified in a desired custom pattern. The printing cycle includes chemistry pickup from a specified well in a well plate, conditioning the sample delivery of the rigid tool by printing a specified number of microdots on a predetermined blotting substrate (e.g., a glass slide), printing the desired microdot configuration on a predetermined optical array, such as, for example, optical fiber bundles, and cleaning the rigid pin printing tool according to a user specified wash cycle before the next chemistry pickup. In a settings menu, a user can specify which wells are used for sample pickup, the stages in a wash cycle, the conditioning procedure, the descent speed of the rigid tool during printing, and the amount of time the tool rests on the printing surface. It is possible to pause the automated routine, make modifications to the pattern or wash cycle, realign the rigid tool and optical array, or manually position the rigid tool before resuming the routine. Spectroscopic measurements can be made using, for example, an imaging spectrometer.

Microdots of the present invention are often micron sized (e.g., less than about 500 microns) but can be nano-sized particles (e.g., about 100 nanometers) of polymer spots that can, but not necessarily are required to, contain an indicator as disclosed herein. Such microdots can also be arranged to include additional layers (i.e., one or more layers) of either a polymer membrane (e.g., a hydrophobic membrane applied to a polymerized microdot that includes an indicator immobilized in a hydrophilic membrane) and/or an indicator immobilized in a polymer (i.e., an indicator chemistry) applied to a polymerized spot. Such an example embodiment in the former case can be a sensor utilized as, for example, a gas sensor. A latter example can include an enzyme immobilized in a membrane with an accompanying indicator in a membrane.

Any of the endoscopic devices and/or elements thereof described herein may be used in conjunction with a system. Endoscopic systems may include multiple elements as outlined herein.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

It is also to be understood that the following claims are intended to cover all of the generic and specific features of the invention herein described, and all statements of the scope of the invention which, as a matter of language, might be said to fall therebetween. Now that the invention has been described.

The present invention will be further illustrated in the following Examples which are given for illustration purposes only and are not intended to limit the invention in any way.

Example 1—Materials and Methods

Subjects ages 8-17 years of age between March 2014 and January 2015 with a defined diagnosis of EoE and who had undergone at least one prior EGD under anesthesia were recruited from the outpatient clinic at Children's Hospital Colorado (CHCO). At the time of the scheduled clinically indicated follow up appointment, subjects were approached if their primary GI provider felt a follow-up esophagoscopy was needed to evaluate their clinical response to therapy. Subjects were queried if they would be interested in having an unsedated TNE with movie distraction performed instead of a sedated EGD. If so, informed consent was obtained and demographic data collected.

Subjects were instructed to not eat or drink for 2 hours prior to the TNE. In a standard clinic room, subjects were asked to sit in a chair designed for outpatient laryngoscopic procedures. Two to six sprays of 4% aerosolized lidocaine were applied to the nares to achieve topical anesthesia. Subject distraction was accomplished using a distraction device 13, such as HMZ-T3 W 3D movie goggles (Sony Corporation, Tokyo, Japan) or Cinemizer Goggles (Carl Zeiss A G, Oberkochen, Germany) dependent on facial size to facilitate viewing an immersive movie or television program of their choice. Parents remained in the room for the duration of the study. For study design purposes and patient comfort one of two designated pulmonologists (ED, RD) or a single otolaryngologist (JP) performed transnasal laryngoscopy using an Olympus BFXP160F 2.8 mm bronchoscope (1.2 mm biopsy channel) in 11/21 subjects and 10/21 subjects using a 4 mm BPMP160F (2 mm biopsy channel) ending with the endoscope in the proximal esophagus. The gastroenterologist (JF) performed esophagoscopy and biopsy collection (3 from proximal and 3 from distal esophagus). Visual confirmation of the adequacy of the biopsy specimens was performed before withdrawing scope. Adverse events, subject symptoms, duration of TNE in 5 minute intervals up to 15 minutes were collected. After the procedure, families were asked to answer the mGHAA-9 (modified Group Health Association of America) endoscopy satisfaction questionnaire and discharged home.

Subjects were called the evening of the procedure and >72 hours later to evaluate for any adverse events. A minimum of two weeks but not greater than 10 weeks after TNE, the subjects and parents were asked to answer an electronic qualitative survey regarding their experience with TNE.

A single pediatric pathologist (KC) evaluated biopsy specimens to assess for size of the sample and inflammatory findings including eosinophil enumeration. To assure adequate high power field (hpf) analysis, the total epithelial surface area used to count eosinophils was analyzed using graphical software and analysis (cellSens Standard, 2013, Olympus America, USA). This was accomplished by comparing the subject's available previous esophageal biopsies using a standard 2.8 mm biopsy forceps to the 1.2 or 2 mm biopsy forceps specimens that were collected during TNE.

Charges from TNEs and subjects' previous isolated sedated EGD were collected to compare the cost of the two procedures. Subjects who underwent combined procedures that may have prolonged sedation such as pH probes, pH impedance probes, colonoscopy, or flexible sigmoidoscopy at their previous endoscopy were excluded from this calculation (n=12). University of Colorado Institutional Review Board (COMIRB-13-2721) approved all study procedures.

Data was recorded into a Red-Cap Secure Database. It is reported as qualitative measure as noted with average, mean, and standard deviation (SD). Surface area analysis to assure adequate specimen size was performed using student's paired, non-parametric, t-test. Charge analysis was performed using unpaired t-test.

Example 2—Evaluation of the Pediatric Nasal Endoscope

Of 22 subjects referred for endoscopy, 22 were contacted and 21 subjects (95.5%) enrolled in this study. One female subject chose not to participate because of "sensory issues." Clinical features of these 21 subjects are shown in Table 1. The average age was 13.04 yrs (+/−2.7 yrs SD, range from 8-17 years). Subject numbers 1, and 13-21 underwent TNE using the 4 mm endoscope and were aged ranging from 8-16 years. Subject numbers 2-12 underwent TNE using the 2.8 mm endoscope and were aged ranging from 10-17 years. The average number of endoscopies previously performed on the subject cohort was 2.19 (SD+/−1.12). All subjects tolerated TNE with no significant adverse events. Duration of TNE procedures decreased as the endoscopists (JF, ED, JP, RD) became more experienced with TNE. (Table 2). The youngest child was 8 years old and was able to tolerate the 4 mm endoscope without difficulty. Symptoms associated with the TNE included gagging and sore throat (Table 3). No adverse event was associated with any emergency department evaluation or unintended evaluation or treatment. One subject had a panic attack prior to the procedure but was still able to complete the TNE without any additional medication. She had a previous history of an anxiety disorder.

Post-procedure assessment revealed a high degree of satisfaction and comfort with the TNE immediately after and at subsequent survey. mGHAA-9 satisfaction instrument average score was 43.19+/−2.6 n=21; maximum 45. A high percentage of subjects reported satisfaction with TNE, child subjects (81%) and parents (90.5%). This is as compared to 81% of combined parent/child subjects satisfied with their previous sedated EGD when asked about it at time of TNE survey. Subjects expressed greater concerns for EGD than TNE on qualitative instrument (61.9% vs. 28.6% respectively). The majority of children (76.2%) would repeat TNE and 100% of parental subjects were willing to have their child undergo the procedure again. More than half of child subjects 52.4% preferred TNE, with 4 subjects not preferring either TNE or sedated EGD, while 85.7% of parental subjects preferred TNE for their child. (Table 4). Reasons for parental preference of TNE included: no anesthesia (61.9%) faster procedure and recovery (52.3%), parental presence during the procedure (28.5%), and lower cost (19%).

Visual TNE findings revealed 11 subjects with normal esophagoscopy, 9 with furrowing and one with furrowing and exudates. Visual findings correlated to the appropriate histologic findings in 85.7% of subjects. In those subjects where visual and histological findings did not correlate, 2 subjects with visual furrowing had normal biopsies, and one with normal appearing mucosa showed histological evidence of eosinophilia <15 eos hpf. (Image 1, Table 5)

Biopsy specimens revealed 12 normal biopsies, 4 with less than 15 eosinophils per hpf, and 5 with greater than 15 eosinophils per hpf. (Table 5, Image 1) No significant difference was identified when comparing total epithelial surface area of TNE biopsies to the biopsy surface area of the matched subject's previous EGD. (Table 5) One subject that was initially evaluated at an outside institution did not have his previous biopsies available for analysis. Total epithelial surface area of mucosal biopsies samples from TNE forceps compared to those obtained with standard endoscopic forceps was not statistically different. (0.33 $mm^2$+/−0.09 vs. 0.38 $mm^2$+/−0.14 mm; p=0.308; n=11; TNE 1.2 mm forceps vs EGD 2.8 mm forceps+/−SD 0.50 mm2+/−0.15 vs. 0.52 mm2+/−0.19; p=0.496, n=9; TNE 2 mm forceps vs EGD 2.8 mm forceps+/−SD). Although there appears to be a surface area difference between the two 2.8 mm control groups (0.38 mm2 and 0.52 mm2), sub-analysis revealed no significant difference was present using unpaired, non-parametric t-test. (p>0.05)

Of the 21 subjects who underwent TNE, 11 had charge data that was comparable and available for analysis. Charges for TNE were calculated to be 60.1% less than sedated EGD with biopsies, including anesthesia, pathology, facility fees, and physician fees.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE 1

Demographics

| Gender (n) | Ethnicity | Age (years) | Average Number of Previous Endoscopies (n) |
|---|---|---|---|
| Male = 13 | Caucasian = 19 | 13.04 | 2.26 |
| Female = 9 | (1 not enrolled) | (SD +/− 2.7) | (SD +/− 1.15) |
| (1 not enrolled) | Native American = 1 | | |
| | Hispanic = 2 | | |

TABLE 2

Duration of TNE

| Gender (n) | Ethnicity | Age (years) | Average Number of Previous Endoscopies (n) |
|---|---|---|---|
| Male = 13 | Caucasian = 19 | 13.04 | 2.26 |
| Female = 9 | (1 not enrolled) | (SD +/− 2.7) | (SD +/− 1.15) |
| (1 not enrolled) | Native American = 1 | | |
| | Hispanic = 2 | | |

TABLE 3

Adverse Events

| Self Reported Symptom | Total Number of Subjects Reporting Symptom |
|---|---|
| Nausea | 4 |
| Choking/Gagging | 12 |
| Sore Throat | 10 |
| Vomiting | 2 |
| Chest Pain | 2 |
| Abdominal Pain | 1 |
| Other | 4 (2 reporting nose discomfort; 2 reporting slightly sore throat) |
| No Significant Symptoms | 7 |

TABLE 4

Satisfaction with the Procedure

| Instrument/Question | Instrument Score |
|---|---|
| mGHAA-9 Score (Max 45 Points) | 43.19 (SD +/− 2.6) |
| Qualitative Satisfaction Instrument | Total Subject of 21 total (n) |
| Child: Satisfaction with TNE | 17 (81%) |
| Parent: Satisfaction with TNE | 19 (90.5%) |
| Parent/Child Satisfied with Sedated EGD | 17 (81%) |
| Parent/Child Concerned with Sedated EGD | 13 (61.9%) |
| Child: Willing to Repeat TNE | 16 (76.2%) |
| Parent: Willing to Repeat TNE | 21 (100%) |
| Child: Prefer to Repeat TNE | 11 (52.4%) - 4 prefer neither EGD or TNE |
| Parent: Prefer to Repeat TNE | 18 (85.7%) - 1 prefer neither EGD or TNE |
| Parent: Qualitative Advantages of TNE | 13/21 - No anesthesia<br>11/21 - Faster procedure and recovery<br>6/21 - Parental presence in the procedure room<br>4/21 - Lower cost |

TABLE 5

TNE Findings

| TNE Findings | Total Specimens (n) |
|---|---|
| Visually Normal | 11 |
| Slight Furrowing | 2 |
| Furrowing | 8 (1 with exudates) |
| Normal Biopsy Abnormality | 12 |
| Eosinophils > 15 hpf | 5 |
| Eosinophils > 15 hpf | 4 |

| Biopsy Forceps | Sample Size | Average Epitheleal Surface Area (mm$^2$) | P-value |
|---|---|---|---|
| EGD 2.8 mm* biopsy forceps | n = 11 | 0.38 (SD 0.14) | P = 0.308 |
| TNE 1.2 mm biopsy forceps | | 0.33 (SD 0.09) | |
| EGD 2.8 mm* biopsy forceps | n = 9 | 0.52 (SD 0.19) | P = 0.496 |
| TNE 2.0 mm biopsy forceps | | 0.50 (SD 0.15) | |

What is claimed is:

1. A method of conducting an unsedated Transnasal Endoscopy exam on a subject, comprising:
   a. providing a distraction device on the subject comprising goggles, comprising:
      providing visual stimuli; and
      providing audio stimuli;
   b. providing a trans-nasal endoscopic device after providing the distraction device, the trans-nasal endoscopic device comprising an inner channel having an inner diameter, wherein the trans-nasal endoscopic device has an outer diameter of less than about 3.5 mm, wherein a ratio of the outer diameter measured in millimeters to the inner diameter measured in millimeters is between 1.5 and 2;
   c. inserting at least a portion of the endoscopic device into a nasal passage of the subject after providing the distraction device on the subject and the subject is in an unsedated state, conducting one or more assessments of a passage of the subject using the endoscopic device, wherein the passage comprises one of an esophagus, a stomach, or an intestine; and visually assessing the esophageal, gastric, or duodenal mucosa in subject;
   d. repeating steps a. through c. on multiple subjects;
      obtaining a satisfaction instrument average score of 43.19+/−2.6 from the subjects based on a modified Group Health Association of America endoscopy satisfaction questionnaire edition by the American Society for Gastrointestinal Endoscopy.

2. The method of claim 1, wherein the distraction device provides an immersive experience.

3. The method of claim 2, wherein the providing visual stimuli and the providing audio stimuli comprises providing a movie, a video, or a television program.

4. The method of claim 3, wherein the one or more assessments of passage of the subject comprises one of procuring samples, capturing and/or recording images, capturing and/or recording video, monitoring, taking measurements, and diagnosing Eosinophilic esophagitis with furrowing in the mucosa or with furrowing and exudates in the mucosa; and performing the Transnasal Endoscopy with the distraction device and performing the one or more assessments within 60 minutes and 90 minutes till the subject is discharged from a hospital or clinic when compared to the time to perform standard esophagogastroduodenoscopy of 3 hours.

5. The method of claim 4, further comprising providing air or water to the passage of the subject using the endoscopic device as needed during use.

6. The method of claim 5, further comprising providing suction to the passage of the subject using the endoscopic device such that air and/or water or body fluids are removed as needed during use.

7. The method of claim 6, further comprising providing a numbing agent to the subject's cavity where the endoscopic device is to be inserted.

8. The method of claim 7, wherein the endoscopic device comprises an imaging device comprising a camera, the camera having a high resolution to capture and/or record images and a high definition to capture and/or record video.

9. The method of claim 8, further comprising recording data from the one or more assessments of the subject into a database.

10. The method of claim 9, further comprising positioning the endoscopic device within the subject using a tip deflection control device, the tip deflection control device comprising a lever, wherein actuation of the lever controls the displacement of a distal end of the endoscope.

11. A method of conducting a Transnasal Endoscopy assessment of a cavity and/or surface of the cavity of subject, comprising: a. providing a trans-nasal endoscopic device comprising an inner channel having an inner diameter of about 2.0 mm to 2.5 mm, wherein the endoscopic device has an outer diameter of less than about 3.5 mm wherein a ratio of the outer diameter measured in millimeters to the inner diameter measured in millimeters is between 1.5 and 2; b. positioning at least a portion of the endoscopic device in the subject through a nasal passage of the subject such that at least an end of the endoscopic device is positioned to visualize the cavity and/or the surface of the cavity of the subject; c. conducting the assessment of the cavity and/or surface of the cavity of the subject using the endoscopic device, wherein the assessment comprises sampling an esophageal mucosa of the subject and visually assessing the mucosa in the cavity in the subject for Eosinophilic esophagitis; d. repeating steps a. through c. on multiple subjects; and e. reporting at least 81% satisfaction with the Transnasal Endoscopy assessment based on a modified Group Health Association of America endoscopy satisfaction questionnaire.

12. The method of claim 11, wherein the plurality of assessments of the subject comprises one of procuring samples, capturing and/or recording images, capturing and/or recording video, monitoring, taking measurements, and the performing the Transnasal Endoscopy with the distraction device within 60 minutes and 90 minutes till subject is discharged from a hospital or clinic when compared to the time to perform standard esophagogastroduodenoscopy of 3 hours.

13. The method of claim 12, further comprising providing air or water to the passage of the subject using the endoscopic device as needed during use.

14. The method of claim 13, further comprising providing suction to the passage of the subject using the endoscopic device such that air and/or water or body fluids are removed as needed during use.

15. The method of claim 14, further comprising providing a numbing agent to the subject's cavity where the endoscopic device is to be inserted.

16. The method of claim 15, wherein the endoscopic device comprises an imaging device comprising a camera, the camera having a high resolution to capture and/or record images and a high definition to capture and/or record video.

17. The method of claim 16, further comprising recording data from the assessment of the subject into a database.

18. The method of claim 17, further comprising positioning the endoscopic device within the subject using a tip deflection control device, the tip deflection control device comprising a lever, wherein actuation of the lever controls the displacement of a distal end of the endoscope.

19. A method of conducting a Transnasal Endoscopy assessment of a cavity and/or surface of the cavity of a subject without general anesthesia, comprising: a. providing the subject with a distraction device comprising goggles, comprising: providing visual stimuli; providing audio stimuli; b. providing an endoscopic device comprising an inner channel extending through a length of the endoscopic device, wherein the endoscopic device has a diameter of less than 4 mm, about 3.5 mm, and the inner channel has an inner diameter of about 2.0 mm to 2.5 mm; c. inserting at least a portion of the endoscopic device through the nasal passage and into an esophagus of the subject after providing the distraction device on the subject; d. conducting the assessment of the esophagus of the subject using the endoscopic device, wherein the assessment comprises sampling an esophageal mucosa of the subject; e. repeating steps a. through d. on multiple subjects; reporting at least 81% satisfaction with the Transnasal Endoscopy assessment based on a modified Group Health Association of America endoscopy satisfaction questionnaire.

20. The method of claim 19, wherein the distraction device provides an immersive experience.

21. The method of claim 20, wherein the providing visual stimuli and the providing audio stimuli comprises providing a movie, a video, or a television program.

22. The method of claim 21, wherein the assessment of the subject comprise one of procuring samples, capturing and/or recording images, capturing and/or recording video, monitoring, taking measurements, and visualizing at least a portion of the esophagus and/or surface of the esophagus of the subject on a viewing device during use.

23. The method of claim 22, further comprising providing air or water to the esophagus of the subject using the endoscopic device as needed during use.

24. The method of claim 23, further comprising providing suction to the esophagus of the subject using the endoscopic device such that air and/or water or body fluids are removed as needed during use.

25. The method of claim 24, further comprising providing a numbing agent to the subject's esophagus where the endoscopic device is to be inserted.

26. The method of claim 25, wherein the endoscopic device comprises an imaging device comprising a camera, the camera having a high resolution to capture and/or record images and a high definition to capture and/or record video.

27. The method of claim 26, further comprising recording data from the assessment of the subject into a database.

28. The method of claim 27, further comprising positioning the endoscopic device within the esophagus using a tip deflection control device, the tip deflection control device comprising a lever, wherein actuation of the lever controls the displacement of a distal end of the endoscopic device.

29. The method of claim 28, further wherein the length of the endoscopic device in between about 0.8 meters to about 1.3 meters.

30. The method of claim 29, further comprising performing the Transnasal Endoscopy with the distraction device and performing the sampling within 60 minutes and 90 minutes till the subject is discharged from a hospital or clinic when compared to the time to perform standard esophagogastroduodenoscopy of 3 hours.

\* \* \* \* \*